(12) United States Patent
Kassim et al.

(10) Patent No.: US 9,072,439 B2
(45) Date of Patent: Jul. 7, 2015

(54) PHOTOPLETHYSMOGRAPHIC DEVICE AND METHODS THEREFORE

(75) Inventors: Md. Irwan bin Md. Kassim, Synapse (SG); Mohamad Sulhede Bin Samsudin, Synapse (SG); Thet Khine Cho, Synapse (SG)

(73) Assignee: Nitto Denko Corporation, Osaka (JP)

( * ) Notice: Subject to any disclaimer, the term of this patent is extended or adjusted under 35 U.S.C. 154(b) by 37 days.

(21) Appl. No.: 13/884,519

(22) PCT Filed: Jan. 5, 2012

(86) PCT No.: PCT/SG2012/000004
§ 371 (c)(1),
(2), (4) Date: Jul. 25, 2013

(87) PCT Pub. No.: WO2012/099536
PCT Pub. Date: Jul. 26, 2012

(65) Prior Publication Data
US 2013/0296665 A1 Nov. 7, 2013

Related U.S. Application Data

(63) Continuation-in-part of application No. 13/010,705, filed on Jan. 20, 2011, now Pat. No. 8,761,853.

(51) Int. Cl.
*A61B 5/1455* (2006.01)
*A61B 5/0295* (2006.01)
*G01N 21/31* (2006.01)
(Continued)

(52) U.S. Cl.
CPC .......... *A61B 5/0295* (2013.01); *G01N 21/3151* (2013.01); *G01N 2021/3144* (2013.01); *A61B 5/7435* (2013.01); *A61B 5/0059* (2013.01); *A61B 2562/0247* (2013.01); *A61B 5/1455* (2013.01);
(Continued)

(58) Field of Classification Search
CPC .. A61B 5/0059; A61B 5/0295; A61B 5/1455; A61B 5/14551; A61B 5/14552; A61B 5/6898; A61B 5/02416; A61B 5/7435
See application file for complete search history.

(56) References Cited

U.S. PATENT DOCUMENTS 4,759,369 A * 7/1988 Taylor ........................... 600/323
4,807,630 A 2/1989 Malinouskas
(Continued)

OTHER PUBLICATIONS

International Search Report issued in PCT/SG2012/000004 mailed Mar. 1, 2012 (2 pages).
(Continued)

*Primary Examiner* — Eric Winakur
(74) *Attorney, Agent, or Firm* — Osha • Liang LLP

(57) ABSTRACT

An optical measurement device and a method for optical measurement are provided. The device comprises an illumination assembly configured to output light to a surface portion of a user for measurement; a detection assembly configured to detect the output light reflected from said surface portion of the user as a signal; an amplifier module coupled to the detection assembly configured to apply a gain to an AC component of the signal; a microcontroller coupled to the detection assembly configured to assess a DC voltage level of the signal; wherein the microcontroller is configured to control the light output at the illumination assembly based on said assessing the DC voltage level; and further wherein the microcontroller is configured to select a gain value for said applying the gain based on said assessing the DC voltage level. Specific embodiments of the device relate to a photoplethysmograph or pulse oximeter.

20 Claims, 22 Drawing Sheets

(51) Int. Cl.
*A61B 5/024* (2006.01)
*A61B 5/00* (2006.01)

(52) U.S. Cl.
CPC .......... *A61B 5/02416* (2013.01); *A61B 5/6898* (2013.01); *A61B 5/14551* (2013.01)

(56) References Cited

U.S. PATENT DOCUMENTS

| | | | |
|---|---|---|---|
| 4,869,254 A | | 9/1989 | Stone et al. |
| 4,892,101 A | * | 1/1990 | Cheung et al. ............... 600/323 |
| 5,112,124 A | * | 5/1992 | Harjunmaa et al. .......... 600/316 |
| 5,365,066 A | * | 11/1994 | Krueger et al. ............... 600/310 |
| 5,632,272 A | | 5/1997 | Diab et al. |
| 5,758,644 A | | 6/1998 | Diab et al. |
| 7,324,848 B1 | | 1/2008 | Turcott |
| 7,499,740 B2 | * | 3/2009 | Nordstrom et al. .......... 600/323 |
| 2009/0024012 A1 | | 1/2009 | Li et al. |
| 2010/0185068 A1 | | 7/2010 | Park et al. |

OTHER PUBLICATIONS

International Preliminary Report on Patentability issued in PCT/SG2012/000004 mailed Aug. 1, 2012 (11 pages).

* cited by examiner

PHOTOPLETHYSMOGRAPHIC DEVICE AND METHODS THEREFORE

CROSS-REFERENCE TO RELATED APPLICATIONS

This application is a national phase application of PCT/SG2012/000004 (hereinafter "international application"), filed on Jan. 5, 2012. The international application claims priority to U.S. patent application Ser. No. 13/010,705 (hereinafter "priority application"), filed on Jan. 20, 2011. The priority application is hereby incorporated by reference in its entirety.

TECHNICAL FIELD

The present invention relates broadly to an optical measurement device and to a method for optical measurement.

BACKGROUND

Optical monitoring of physiological characteristics utilizes the detection of light transmitted through a location of a user being measured. Photoplethysmography (PPG) is an optical measurement technique used to detect blood volume changes in the microvascular bed of living tissue, typically by detecting light transmitted through the ear lobe or fingertip. As arterial pulsations enter the capillary bed, changes in the volume of the blood vessels or characteristics of the blood itself modify the optical properties of the capillary bed. A PPG signal is used to measure saturation of peripheral oxygen (SpO2), which is an estimation of the level of oxygen saturation in a fluid, such as blood. The PPG signal can also be used to measure blood pressure.

A device such as a pulse oximeter provides for measuring enhanced optical pulsatile signals emitted by the changes in the volume of blood flowing through a user. The pulse oximeter typically has a pair of small light emitting diodes (LEDs) facing a photodiode/photodetector, with a translucent part of the user's body, usually a fingertip or an earlobe, positioned there between. The LEDs illuminate the tissue (e.g. skin) of the user and the photodetector measures small variations in light intensity associated with changes in perfusion in a catchment volume. An oximeter in such a configuration is typically called a transmittance-type oximeter. The light from the LEDs passes through the tissue and is detected by the photodiode. One LED is red, with wavelength of approximately 660 nanometers (nm), and the other is infrared, with a wavelength of approximately 905, 910 or 940 nm. Absorption at these wavelengths differs significantly between oxyhemoglobin and its deoxygenated form. Therefore, the ratio of oxyhemoglobin to deoxyhemoglobin can be calculated from the ratio of the absorption of the red and infrared light, i.e. the ratio of red light to infrared light absorption of pulsating components at the measuring site.

For transmittance-type oximeters, a cuff or holder is typically provided to function primarily as a holder for the photodiode and also as a shield against ambient light.

On the other hand, apart from transmittance-type oximeters, there also exist reflectance-type oximeters. For reflectance-type oximeters, the LEDs and the photodiode reside on the same side of the translucent part of the user's body. Light from the LEDs are reflected from the portion to be measured and detected by the photodiode. For reflectance-type oximeters, ambient light can be a significant factor in accuracy of light detection by the photodiode. Thus, reflectance-type oximeters typically still require a cuff or a holder/clip to provide shielding against ambient light from interfering with reflected light from the LEDs.

Furthermore, for certain types of reflectance-type oximeters without clips, such as those in patch form, a shield is still required on the base of the oximeter to provide the ambient light shielding.

One problem typically faced by users is a situation whereby a user has low blood flow in capillaries of the user portion to be measured. Such a situation is typically termed a low perfusion or "cold finger" scenario. The raw PPG signals obtained in such situations have large direct-current (DC) components and in comparison, very small alternating-current (AC) components. Typically, for such situations, oximeters can provide only a limited gain, as the large DC components can lead to non-readings/saturation with larger gains. Thus, with small gains, the AC components obtained typically provide inaccurate readings.

Thus, in view of the above, there exists a need for an optical measurement device and method that seek to address at least one of the above problems.

SUMMARY

In accordance with an aspect of the present invention, there is provided an optical measurement device, the device comprising an illumination assembly configured to output light to a surface portion of a user for measurement; a detection assembly configured to detect the output light reflected from said surface portion of the user as a signal; an amplifier module coupled to the detection assembly configured to apply a gain to an alternating-current component of the signal; a microcontroller coupled to the detection assembly configured to assess a direct-current voltage level of the signal; wherein the microcontroller is configured to control the light output at the illumination assembly based on said assessing the direct-current voltage level; and further wherein the microcontroller is configured to select a gain value for said applying the gain based on said assessing the direct-current voltage level.

The microcontroller may be configured to determine that a measurement is a low perfusion measurement based on said assessing the direct-current voltage level, and wherein if there is a low perfusion measurement, the microcontroller may control the light output at the illumination assembly to a lower intensity than that producing the present direct-current voltage level and may select a large gain value as compared to normal measurements for said applying the gain.

The illumination assembly may comprise a red light source and/or an infra-red light source.

The light sources may be toggled on/off for the detection assembly to detect the reflected output light as a single signal.

An amplitude difference between a maximum point and a minimum point of the single signal may be maintained below a predetermined level by the microcontroller controlling the light output at the illumination assembly.

The predetermined level may be obtained based on the alternating-current component of the signal being within a saturation level, upon the amplifier module applying the gain.

The device may further comprise a summing amplifier coupled to the amplifier module, the summing amplifier may be configured to move the alternating-current component of the signal above a ground voltage level.

The saturation level may be based on an output of the summing amplifier.

The large gain value may be about 20 to 30 times.

In accordance with another aspect of the present invention, there is provided a method for optical measurement, the method comprising outputting light to a surface portion of a user for measurement; detecting the output light reflected from said surface portion of the user as a signal; applying a gain to an alternating-current component of the signal; assessing a direct-current voltage level of the signal; controlling the light output at the illumination assembly based on said assessing the direct-current voltage level; and selecting a gain value for said applying the gain based on said assessing the direct-current voltage level.

The method may further comprise determining that a measurement is a low perfusion measurement based on said assessing the direct-current voltage level, and wherein if there is a low perfusion measurement, the method may further comprise controlling the light output to a lower intensity than that producing the present direct-current voltage level and selecting a large gain value as compared to normal measurements for said applying the gain.

The step of outputting light may comprise using a red light source and/or an infra-red light source.

The method may further comprise toggling the light sources on/off for the reflected output light to be detected as a single signal.

The method may further comprise maintaining an amplitude difference between a maximum point and a minimum point of the single signal below a predetermined level by said controlling the light output at the illumination assembly.

The predetermined level may be obtained based on the alternating-current component of the signal being within a saturation level, upon said applying the gain.

The method may further comprise using a summing amplifier to move the alternating-current component of the signal above a ground voltage level.

The saturation level may be based on an output of the summing amplifier.

The large gain value may be about 20 to 30 times.

In accordance with another aspect of the present invention, there is provided a computer readable data storage medium having stored thereon computer code means for instructing a microcontroller of an optical measurement device to execute a method for an optical measurement, the method comprising outputting light to a surface portion of a user for measurement; detecting the output light reflected from said surface portion of the user as a signal; applying a gain to an alternating-current component of the signal; assessing a direct-current voltage level of the signal; controlling the light output at the illumination assembly based on said assessing the direct-current voltage level; and selecting a gain value for said applying the gain based on said assessing the direct-current voltage level.

For the computer readable data storage medium, the method may further comprise determining that a measurement is a low perfusion measurement based on said assessing the direct-current voltage level, and wherein if there is a low perfusion measurement, the method may further comprise controlling the light output to a lower intensity than that producing the present direct-current voltage level and selecting a large gain value as compared to normal measurements for said applying the gain.

BRIEF DESCRIPTION OF THE DRAWINGS

Example embodiments of the invention will be better understood and readily apparent to one of ordinary skill in the art from the following written description, by way of example only, and in conjunction with the drawings, in which.

DETAILED DESCRIPTION

The example embodiments described herein can provide an optical measurement device and method that can obtain a photoplethysmography (PPG) signal from a user in a low perfusion scenario. The measurements in the example embodiments are non-invasive optical physiological measurements. In the example embodiments, DC signals can be made available for saturation of peripheral oxygen (SpO2) calculations/measurements.

In an example implementation, an optical measurement device is used for illuminating a surface portion of the user and detecting reflected light from the surface portion. The measurement device can transmit the detected light information to another device, for e.g. a personal mobile processing device, to carry out further processing, e.g. for removal of ambient light interference for SpO2 values determination.

Before proceeding to more fully describe some example embodiments, it may be beneficial to briefly describe components of a PPG signal.

Figure 1:
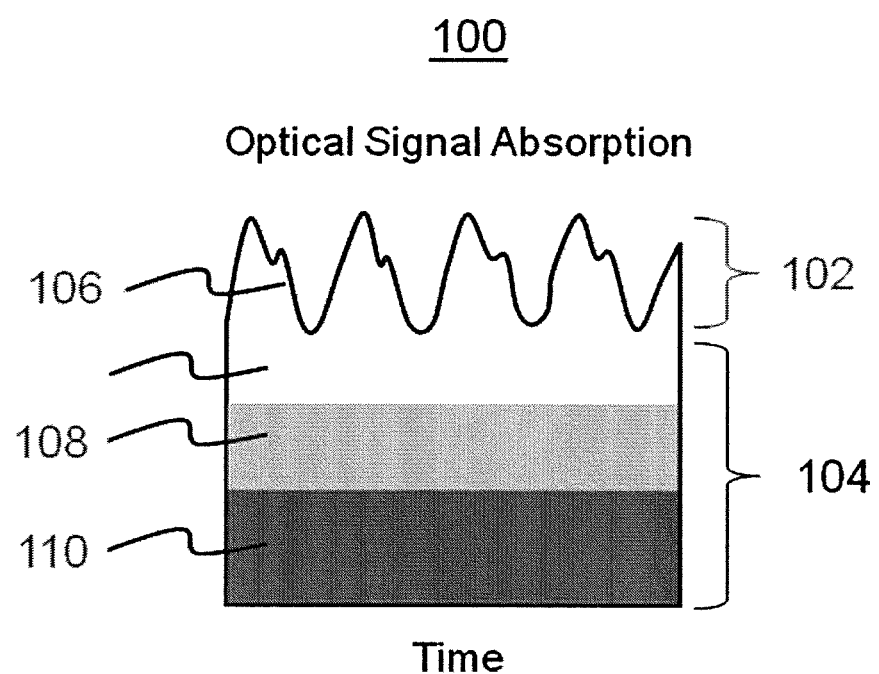
FIG. 1 illustrates a graphical representation of a photoplethysmograph (PPG) signal.
Figure 2:
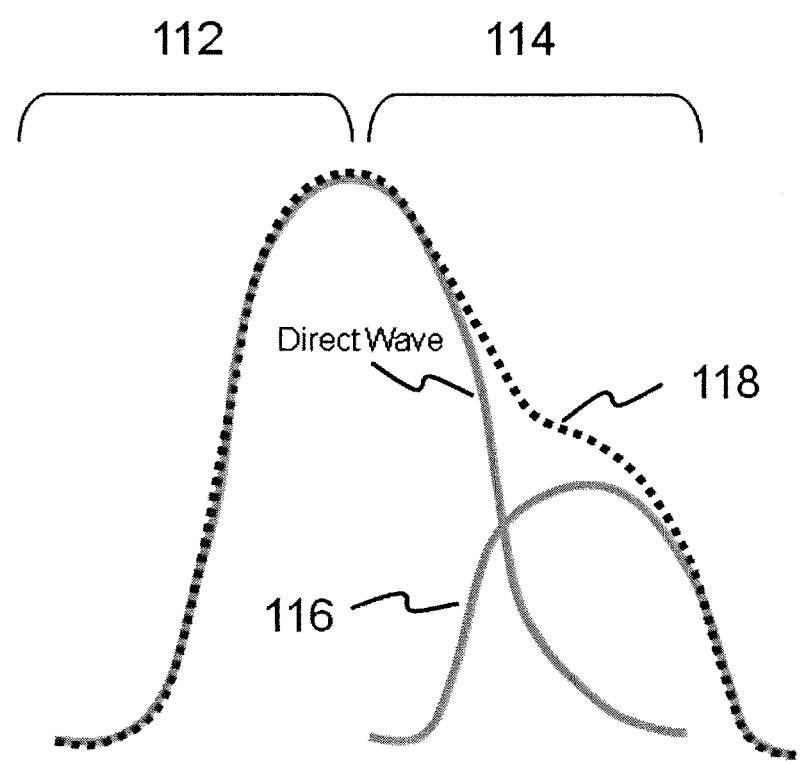
FIG. 2 is an illustration of an alternating current (AC) pulse waveform of a PPG signal.

FIGS. 1 and 2 are provided to briefly describe components of a PPG signal. FIG. 1 illustrates a graphical representation of a photoplethysmograph (PPG) signal 100, which can generally be divided into two components: an AC component 102 due to the absorption of light in pulsatile arterial blood volume 106; and a DC component 104 caused by the absorption produced by non-pulsatile arterial blood—i.e. venous blood and capillary blood 108, and tissue absorption 110.

In FIG. 1, this AC component 102 is superimposed onto a large quasi-DC component 104 that relates to the tissues and to the average blood volume. This DC component 104 varies slowly due to respiration, vasomotor activity and vasoconstrictor waves. With suitable electronic filtering and amplification, both the AC component 102 and DC component 104 can be extracted for subsequent pulse wave analysis.

Two significant characteristics of the PPG AC pulse waveform 102 have been described and are illustrated in FIG. 2, where the appearance of the pulse waveform was defined as two phases: a first anacrotic phase 112 being the rising edge of the pulse, and a second catacrotic phase 114 being the falling edge of the pulse. The first phase 112 is primarily concerned with systole, while the second phase 114 represents diastole and wave reflections 116 from the periphery. A dicrotic notch 118 is usually seen in the second catacrotic phase 114 of subjects with healthy compliant arteries.

In the following detailed description, reference will be made to the accompanying drawings. The aforementioned accompanying drawings show by way of illustration and not by way of limitation, specific embodiments and implementations consistent with principles of the present invention. These implementations are described in sufficient detail to enable those skilled in the art to practice the invention, and it is to be understood that other implementations may be utilized and that structural changes and/or substitutions of various elements may be made without departing from the scope of the present invention. The following detailed description is, therefore, not to be construed in a limited sense. Additionally, the various embodiments as described may be implemented in the form of software running on a general purpose computer, in the form of a specialized hardware, or combination of software and hardware.

The terms "coupled" or "connected" as used in this description are intended to cover both directly connected or connected through one or more intermediate means, unless otherwise stated.

The description herein may be, in certain portions, explicitly or implicitly described as algorithms and/or functional operations that operate on data within a computer memory or an electronic circuit. These algorithmic descriptions and/or functional operations are usually used by those skilled in the information/data processing arts for efficient description. An algorithm is generally relating to a self-consistent sequence of steps leading to a desired result. The algorithmic steps can include physical manipulations of physical quantities, such as electrical, magnetic or optical signals capable of being stored, transmitted, transferred, combined, compared, and otherwise manipulated.

Further, unless specifically stated otherwise, and would ordinarily be apparent from the following, a person skilled in the art will appreciate that throughout the present specification, discussions utilizing terms such as "scanning", "calculating", "determining", "replacing", "generating", "initializing", "outputting", and the like, refer to action and processes of a instructing processor/computer system, or similar electronic circuit/device/component, that manipulates/processes and transforms data represented as physical quantities within the described system into other data similarly represented as physical quantities within the system or other information storage, transmission or display devices etc.

The description also discloses relevant device/apparatus for performing the steps of the described methods. Such apparatus may be specifically constructed for the purposes of the methods, or may comprise a general purpose computer/processor or other device selectively activated or reconfigured by a computer program stored in a storage member. The algorithms and displays described herein are not inherently related to any particular computer or other apparatus. It is understood that general purpose devices/machines may be used in accordance with the teachings herein. Alternatively, the construction of a specialized device/apparatus to perform the method steps may be desired.

In addition, it is submitted that the description also implicitly covers a computer program, in that it would be clear that the steps of the methods described herein may be put into effect by computer code. It will be appreciated that a large variety of programming languages and coding can be used to implement the teachings of the description herein. Moreover, the computer program if applicable is not limited to any particular control flow and can use different control flows without departing from the scope of the invention.

Furthermore, one or more of the steps of the computer program if applicable may be performed in parallel and/or sequentially. Such a computer program if applicable may be stored on any computer readable medium. The computer readable medium may include storage devices such as magnetic or optical disks, memory chips, or other storage devices suitable for interfacing with a suitable reader/general purpose computer. The computer readable medium may even include a wired medium such as exemplified in the Internet system, or wireless medium such as exemplified in bluetooth technology. The computer program when loaded and executed on a suitable reader effectively results in an apparatus that can implement the steps of the described methods.

The example embodiments may also be implemented as hardware modules. A module is a functional hardware unit designed for use with other components or modules. For example, a module may be implemented using digital or discrete electronic components, or it can form a portion of an entire electronic circuit such as an Application Specific Integrated Circuit (ASIC). A person skilled in the art will understand that the example embodiments can also be implemented as a combination of hardware and software modules.

In some example embodiments, saturation of peripheral oxygen (SPO2) information of a user is derivable from detected output light information from both a red LED and an infra-red LED. Further, in the description herein, the term "light" as used herein is meant to be interpreted in a broad sense and is not limited to visible light only. The term "light" as used herein can include, but is not limited to, X-ray light rays, visible light rays, ultraviolet light rays and infra-red light rays.

Figure 3:
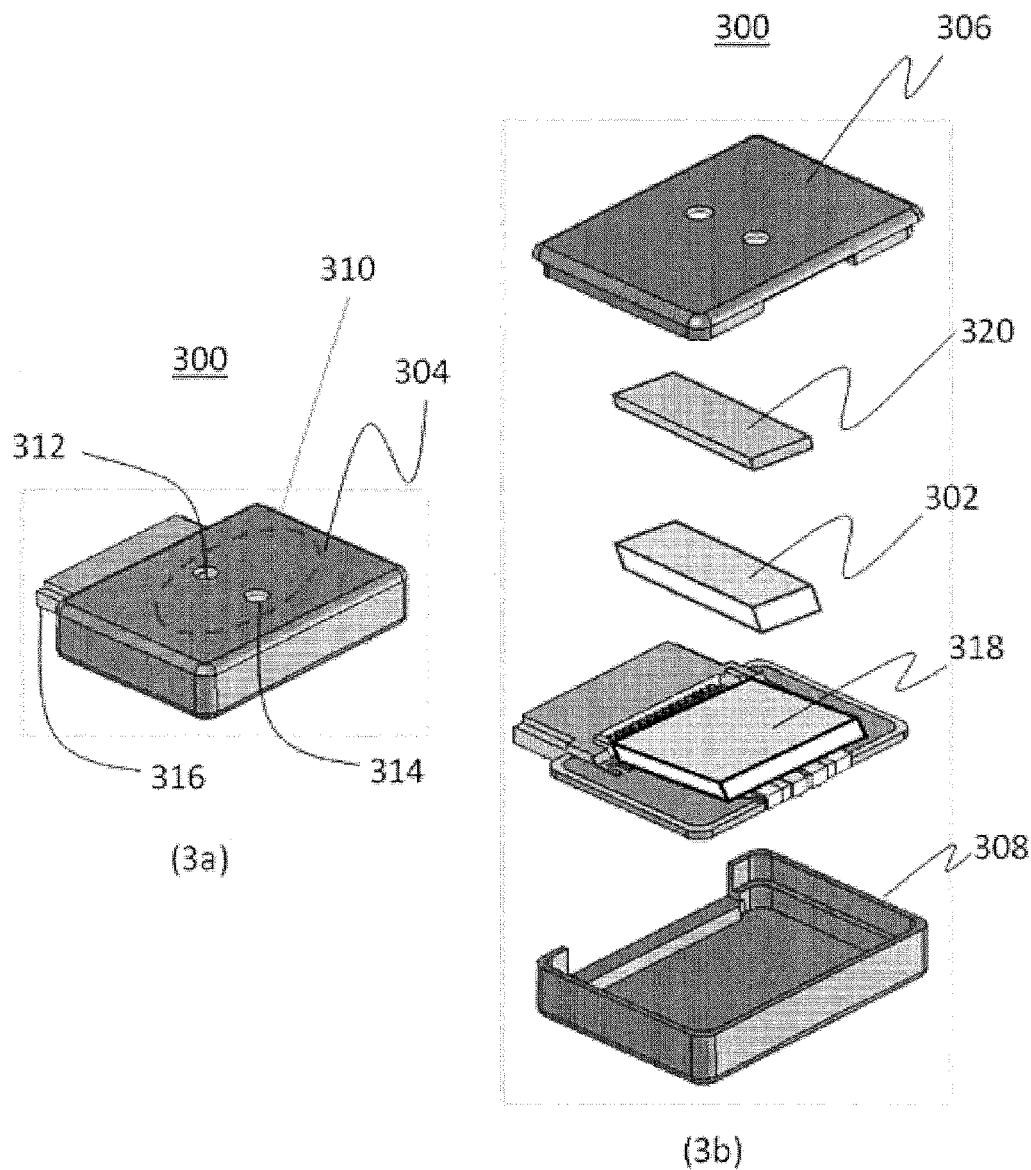
FIG. 3(a) is a schematic illustration of an optical measurement device in an example embodiment.
FIG. 3(b) shows schematically an exploded view of the optical measurement device.
FIG. 3(c) is a diagram illustrating optical transmission characteristics of optical filtering in an example embodiment.
Figure 3:
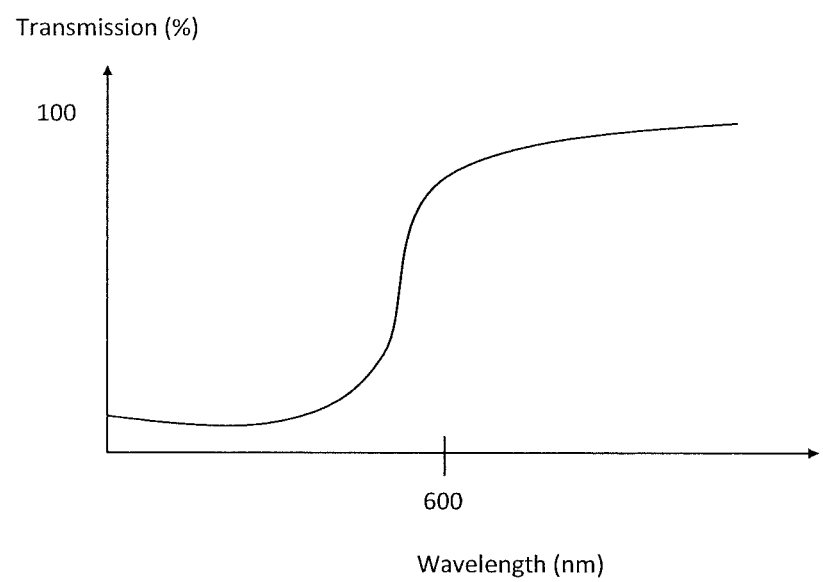

FIG. 3(a) is a schematic illustration of an optical measurement device in an example embodiment. FIG. 3(b) shows schematically an exploded view of the optical measurement device.

The optical measurement device 300 is a reflectance-based device in the example embodiment. The optical measurement device 300 comprises an illumination and detection assembly 302 encased in a housing 304. In the exploded view in FIG. 3(b), the housing 304 is shown divided into a top casing 306 and a base casing 308. The top casing 306 comprises a measurement surface 310, shown schematically with dotted lines. The measurement site/surface 310 is coupled to a light source 312 and one or more light detectors e.g. 314 of the illumination and detection assembly 302. The optical measurement device 300 further comprises a coupling member 316 that can provide coupling between the measurement device 300 to a personal mobile processing device/feedback unit (not shown) in a cableless configuration. The coupling member 316 may be in the form of an interface port such as a universal serial bus (USB) port or the 30 pin connection used in the Apple® iPhone® (Apple Computer, Inc., Cupertino, Calif.) etc.

In one exemplary embodiment, the feedback unit may be a portable device, such as a mobile phone, smartphone, personal digital assistant (PDA), tablet, netbook or laptop, although this list is not exhaustive by any means. However, the feedback unit may not need to be portable, and could similarly be a computer or server. The feedback unit may be connected with the device 300 in a wired or wireless fashion, or through a proprietary connector, such a universal serial bus (USB) port or the 30 pin connection used in the Apple® iPhone® (Apple Computer, Inc., Cupertino, Calif.).

In the example embodiment, the light source 312 can propagate light through a surface portion of a user for measurement, e.g. a portion of living tissue of the user placed at the measurement site. The light detectors e.g. 314 can detect light reflected from the portion of living tissue of the user. The detected light information at the light detectors e.g. 314 can be transmitted via the coupling member 316 to a personal mobile processing device (not shown), for example, for further processing.

In the example embodiment, optionally, a pressure detection assembly 318 may be provided in the optical measurement device 300. The pressure detection assembly 318 can be configured to detect and transmit to a personal mobile processing device (not shown) an amount of pressure applied by a body part of a user to the measurement device 300 during optical measurement. The pressure information can be used, for example but not limited to, to detect whether a body part has been placed on the measurement device and/or whether the pressure exerted by a body part is sufficient for accurate readings to be obtained.

The optical measurement device 300 can additionally be integrated with optical filters e.g. 320 to minimize the disturbance from ambient light. In the example embodiment, an edge filter with optical transmission characteristics can be used.

FIG. 3(c) is a diagram illustrating optical transmission characteristics of optical filtering in an example embodiment. In this example embodiment, wavelengths of light below about 600 nm is filtered out and prevented from reaching the light detectors e.g. 314. This can be effective as the wavelengths of interest are that of e.g. about 600 nm and about 940 nm only. Alternatively, filters which target specific wavelengths of interest can be used. For example, filters which, e.g. when used in combination, allow transmission of light from about 600-700 nm, and about 900-1000 nm can be used. Alternatively, a single filter which allow transmission of light from about 600-1000 nm can be used alone.

Figure 4A:
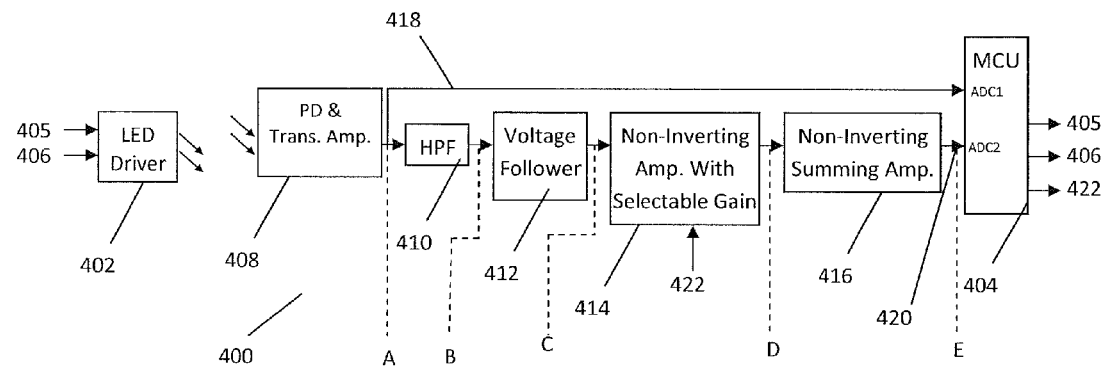
FIG. 4(a) is a schematic block diagram illustrating an optical measurement device in an example embodiment.
Figure 4B:
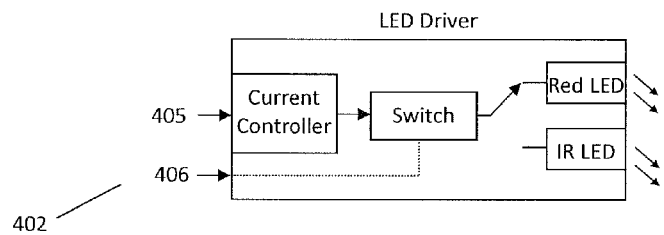
FIG. 4(b) is a schematic block drawing illustrating an illumination assembly in an example embodiment.
Figure 4C:
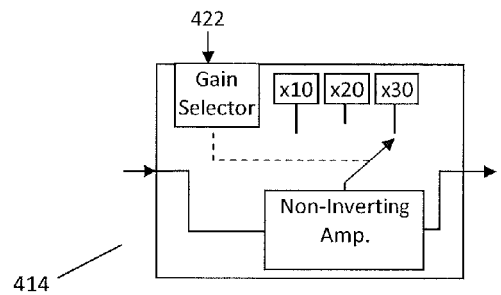
FIG. 4(c) is a schematic block drawing illustrating a non-inverting amplifier with selectable gain in an example embodiment.

FIG. 4(a) is a schematic block diagram illustrating an optical measurement device 400 in an example embodiment. FIG. 4(b) is a schematic block drawing illustrating an illumination assembly in an example embodiment. FIG. 4(c) is a schematic block drawing illustrating a non-inverting amplifier with selectable gain in an example embodiment. An illumination assembly 402 is provided for propagating light through a surface portion of a user for measurement. The illumination assembly 402 can comprise one or more light sources e.g. light emitting diodes (LEDs) that can vary in light intensity based on variable resistors and controlled by a microcontroller MCU 404 (see control at numeral 405). In the example embodiment, the MCU 404 may also control the activation of the one or more light sources e.g. Red or IR LED, via the control at numeral 406. A detection assembly 408 is provided to detect light reflected/transmitted off the surface portion of the user. The detection assembly 408 can comprise a photodetector (PD) coupled to a transimpedance amplifier. The detection assembly 408 is coupled to a high-pass filter 410 that is in turn coupled to a voltage follower amplifier module 412. The high-pass filter 410 can be implemented using a capacitor and a resistor. The voltage follower amplifier module 412 is coupled to a non-inverting amplifier module 414 that can provide a selectable gain. As shown in FIG. 4(c), the gain is selectable between a number of possible gain options, with the selection being controlled by the MCU 404 via the control signal 422. The non-inverting amplifier module 414 is coupled to a non-inverting summing amplifier module 416 that can provide a unity gain.

As seen in FIG. 4(a), ADC1 418 provides the DC portion of a measured signal and ADC2 420 provides the AC portion of a measured signal.

In the example embodiment, the LEDs illumination intensity can be adjusted based on feedback at the MCU 404. The MCU 404 can adjust the respective current (at 405) to the LEDs so as to obtain respective raw PPG signals which are as close as possible in amplitude at point A, and e.g. between about 2-2.5V at the detection assembly 408. In the example embodiment, the LEDs can comprise a red LED and an infrared LED. Each LED can be individually adjusted in illumination intensity.

During operation, at the output of the detection assembly 408, a raw PPG signal is recorded. This enables the DC component of the signal to be acquired e.g. for LED illumination intensity adjustment and SpO2 calculation. The high-pass filter 410 can introduce a filter with a high-pass cut off of e.g. about 0.12 Hz so as to remove the DC component of the raw PPG signal. This can also produce the AC component of the signal, with the AC component oscillating about ground voltage. The output of the high-pass filter 410 is transmitted to the voltage follower amplifier module 412 to create a high impedance signal. The inventors have recognised that without a high impedance, the signal may be lost at the amplification stage subsequently.

In the example embodiment, the high impedance signal undergoes amplification at the non-inverting amplifier module 414. In the example embodiment, a gain can be introduced to the signal. The gain can be selected from a plurality of gain factors such as 10 times, 20 times or 30 times. For each gain factor, a low pass filter of e.g. about 318 Hz can be introduced. Following the selection of a suitable gain, the signal is transmitted to the non-inverting summing amplifier module 416. A DC value of about 1.5V is added to the signal so that the signal is significantly above ground voltage. A unity gain is provided with an integrated low pass filter of about 318 Hz.

Figure 5:
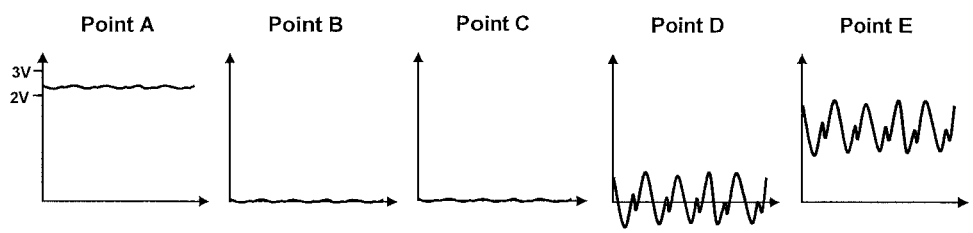
FIG. 5 is a schematic flow graph diagram illustrating signal conditioning for a single detected signal in an example embodiment.

FIG. 5 is a schematic flow graph diagram illustrating signal conditioning for a single detected signal in an example embodiment. Reference is also made to FIG. 4. The signal is detected at the detection assembly 408. The signal may be either a Red signal or an IR signal detected from a red LED illumination or a IR LED illumination respectively. The graph at Point A shows the signal with both DC and AC components at the output of the detection assembly 408. It can be seen that the AC component is small from the graph. The graph at Point B shows the signal at the output of the high-pass filter 410 with the DC component of the signal removed and the AC component of the signal being forced to oscillate about ground voltage. The graph at Point C shows the high impedance AC signal at the output of the voltage follower amplifier module 412. The graph at Point D shows the AC signal at the output of the non-inverting amplifier module 414 with a suitable gain provided to the signal. The graph at Point E shows the AC signal at the output of the non-inverting summing amplifier module 416. A DC value of about 1.5V has been added to the AC signal such that the signal is pushed above the ground voltage. This can advantageously allow the signal to be digitized by the analog-to-digital converter of the microcontroller 404.

Further to the above, it has been recognized by the inventors that, to provide a single path system, control of the illumination intensities of the respective light sources (e.g. the LEDs) and/or selection of gain can be significant in obtaining accurate measurements and avoiding saturation at the output.

FIG. 6(*a*) is a schematic graphical illustration of output obtained at a light detector (compare 408 of FIG. 4) during a light emitting diode (LED) firing sequence in an example embodiment. During an Ambient (Am) or OFF condition 602, both the IR and RED LEDs are turned off, and an ambient PPG signal 604 can be obtained. During a toggling sequence 606, the IR and RED LEDs are alternatingly turned on. The MCU can then perform time based de-multiplexing to extract the respective IR and RED PPG signals.

FIG. 6(*b*) shows an example of de-multiplexed signals in an example embodiment. The de-multiplexed signals can be obtained during the toggling phase at the various points in the signal processing path. The IR PPG signals (in bold) e.g. 612 and Red PPG signals (dotted) e.g. 614 can be obtained.

FIG. 6(*c*) shows another example of de-multiplexed signals in an example embodiment. FIG. 6(*c*) is similar to FIG. 6(*b*) with the exception that the time scale used for FIG. 6(*c*) is smaller. Compare t1-t2 indicated on FIGS. 6(*b*) and (*c*). The graphs of FIG. 6(*c*) represent the individual sampled points, rather than the complete waveforms formed by the individual points as shown in FIG. 6(*b*). A more detailed illustration is provided below with reference to FIG. 16.

Figure 6A:
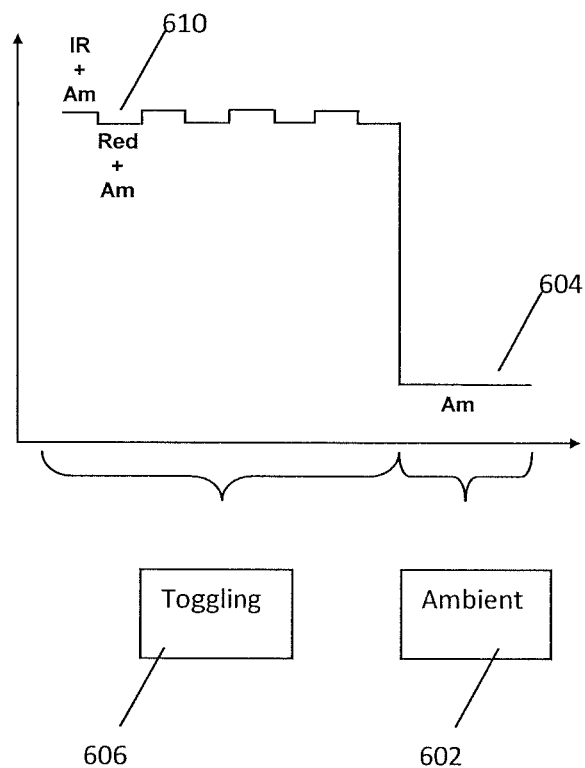
FIG. 6(a) is a schematic graphical illustration of output obtained at a light detector during a light emitting diode (LED) firing sequence in an example embodiment.
Figure 6B:
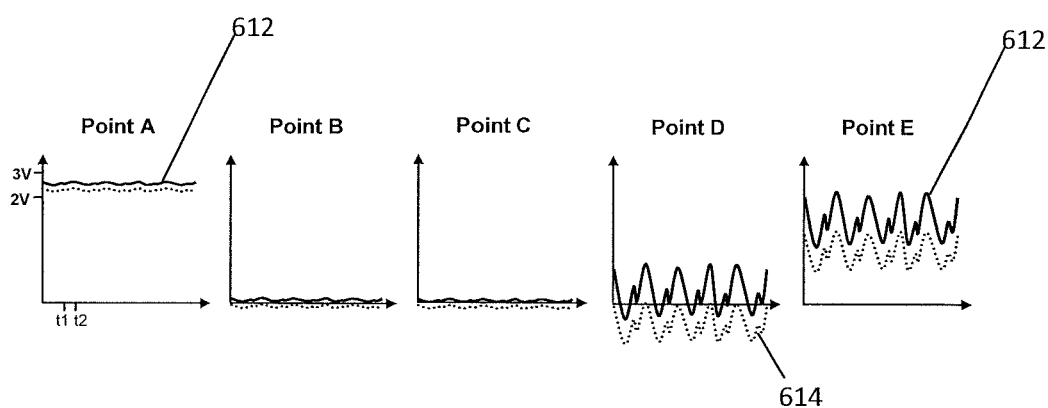
FIG. 6(b) shows an example of de-multiplexed signals in an example embodiment.
Figure 6C:
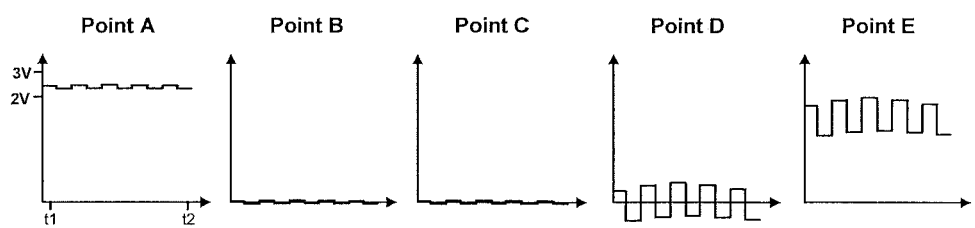
FIG. 6(c) shows another example of de-multiplexed signals in an example embodiment.
Figure 7:
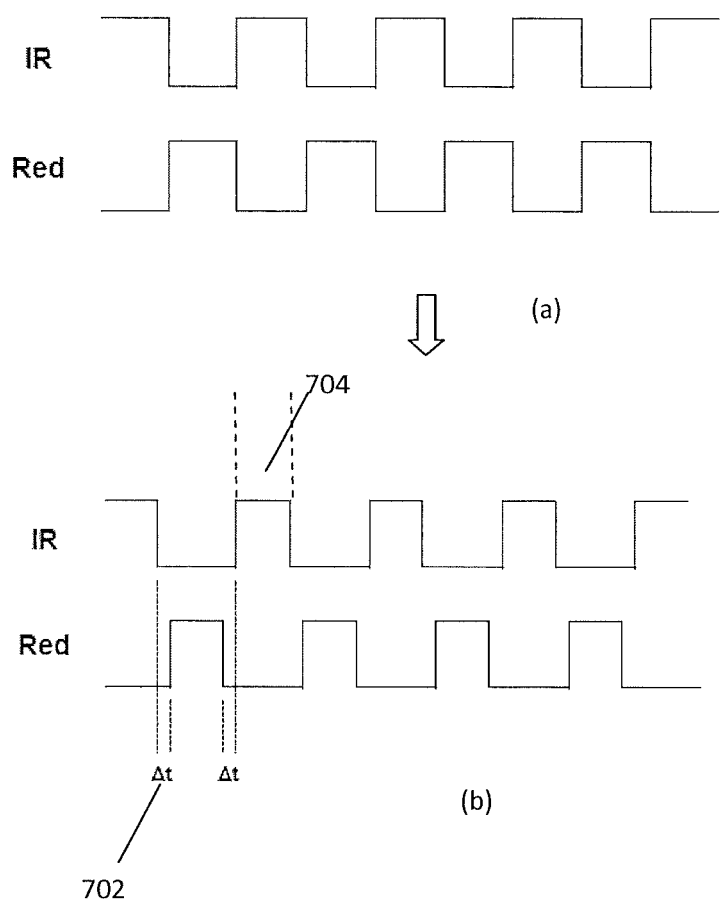
FIG. 7(a) is a schematic timing wave diagram for toggling on/off of an infra-red (IR) LED and a red (Red) LED in an example embodiment.
FIG. 7(b) is an alternative schematic timing wave diagram for toggling on/off of an IR LED and a Red LED in an example embodiment.

FIG. 7(*a*) is an exemplary schematic timing wave diagram for toggling on/off of an IR LED and a Red LED. FIG. 7(*b*) is an alternative schematic timing wave diagram for toggling on/off of an IR LED and a Red LED in an example embodiment. FIG. 7(*b*) is a modification of FIG. 7(*a*) to allow an ambient PPG signal to be obtained. FIG. 7(*b*) also illustrates a toggling sequence within sequence 606 of FIG. 6. There is a relatively brief period Δt 702 between each toggling, e.g. about 100 μs, when both the Red and IR LEDs are turned off. Each LED is turned on for about 2.9 ms e.g. numeral 704, which makes each toggling cycle to be about 6 ms. This can improve the IR and Red PPG signals accuracy. The brief period Δt 702 allows a time break between switching from a Red and IR signal condition (or vice versa). This may be useful to a single path system whereby detection of the red and IR signals are performed using the same circuitry, i.e. a single path system. The brief period Δt 702 introduced can ensure that each detected Red and IR light information displays its own behavior. The inventors have recognised that if there is no break e.g. provided by period Δt 702, the light signal of the previously switched on LED may still be present in the processing path. That is, using the brief period can reduce "crosstalk" issues.

FIG. 8(*a*) is a schematic graph illustrating output obtained at a light detector (compare 408 of FIG. 4) during toggling between a red LED and an IR LED in an example embodiment. The graph is shown with the y-axis representing voltage V values and the x-axis representing milli-seconds ms values. The red LED and IR LED are preferably driven by the microcontroller so that the detected output (compare point A of FIG. 4(*a*)) based on the respective red and IR LEDs is at the same voltage of about 2.5V. However, it is appreciated that this is often difficult and there may be differences in the outputs. FIG. 8(*a*) shows a corresponding amplitude difference of about 100 mV. The oscillation period corresponds to the toggling period, e.g. with respect to FIG. 7(*a*).

In some example embodiments, the intensity of each IR and Red LED is further tuned such that the output at the detection assembly shows a response of between 2V-2.5V (at ADC1). That is, the inventors have recognized that the effects of ambient light signals can be reduced as much as possible by tuning the intensities of the IR and Red LEDs to be maximized as long as the detection assembly has not reached saturation. In the example embodiment, the saturation voltage is based on the Vcc used and is about 3.3V. In the example embodiment, a detected output of about 2.5V is considered optimal as this can provide for a signal amplitude that is as high as possible above the ambient signal, but still provide room for the signal to not be saturated at 3.3V.

Thus, the inventors have recognized that ambient light interference can be minimized as compared to the IR and Red signals detected. Thus, in the example embodiment, detection of the ambient signal can be conducted in its own ambient detection period before or after the toggling sequence of the IR and Red light sources.

Further, the inventors have recognized that it is significantly beneficial to maintain the DC components of the Red and the IR outputs to be set as close as possible in the single path approach. Otherwise, obtaining a good PPG signal from a person with low perfusion by setting a high gain may not be possible, due to signal saturation at later stages of the signal processing path, such as saturation at the non-inverting summing amplifier module (compare 416 of FIG. 4). An example saturation voltage level is about 3.3V.

The inventors have recognized that, for a normal measurement scenario, a gain of about 10 times at the non-inverting amplifier module (compare 414 of FIG. 4) may be used. For low perfusion scenarios, a higher gain of about 20 or 30 may be used, given the lower amplitude of the AC signals detected. The inventors have verified the above in a number of experiments.

As a further explanation, with an initial detected amplitude difference of about 100 mV, and with a gain of 10 times, the amplitude difference is amplified to about 1V upon signal conditioning using the circuit shown in FIG. 4.

Figure 8A:
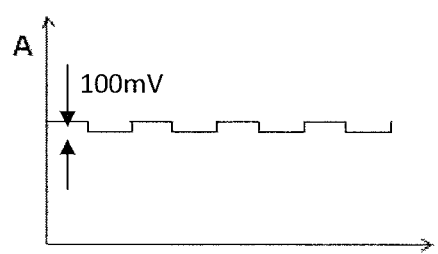
FIG. 8(a) is a schematic graph illustrating output obtained at a light detector during toggling between a red LED and an IR LED in an example embodiment.
Figure 8B:
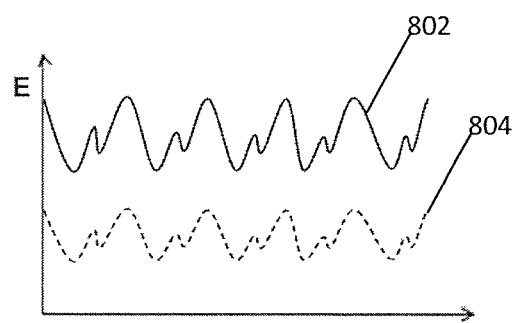
FIG. 8(b) is a schematic graph illustrating the amplified output of FIG. 8(a) in an example embodiment.

FIG. 8(b) is a schematic graph illustrating the demultiplexed amplified output of FIG. 8(a) in an example embodiment. The output is sampled at e.g. point E of FIG. 4(a). It is appreciated that the AC components are not immediately visible from the graph of FIG. 8(a) as the DC components are much larger in amplitude. However, as the signal propagates through the various stages referenced by e.g. numerals 410, 412, 414 and 416, (e.g. from point A to point E of FIG. 4(a)), the DC component is removed leaving only amplified AC components of the Red and IR PPG signals. With appropriate de-multiplexing, an IR PPG signal (solid lines) e.g. 802 and a Red PPG signal (dotted lines) e.g. 804 can be observed. FIGS. 8(a) and 8(b) correspond to the point A graph for FIG. 6(c) and the point E graph for FIG. 6(b) respectively. As can be further observed, the gap in FIG. 8(b) is about 1V after the signal conditioning, e.g. at Point E of FIG. 4(a), at the output of the non-inverting summing amplifier module (compare 416 of FIG. 4).

Therefore, for a low perfusion scenario, where a higher gain of e.g. 20 times, the gap between the Red and IR PPG AC signals can be about 2V, i.e. the entire signal waveform can reach saturation relatively easily, either at the top amplitude or bottom amplitude.

Figure 9:
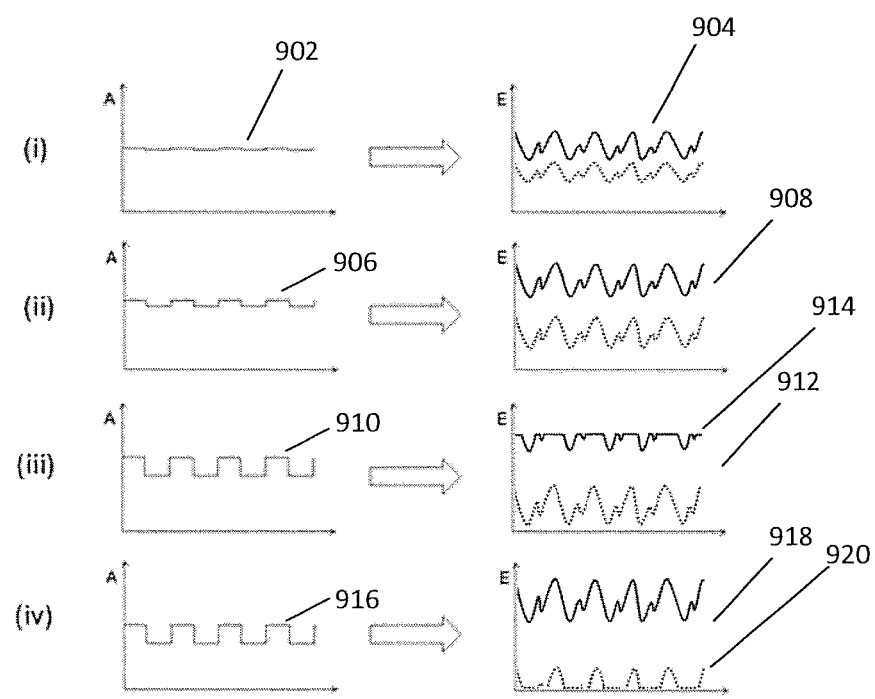
FIG. 9 is a series of schematic graph diagrams illustrating different output scenarios by keeping a constant gain of about 10 times and varying the amplitude differences of detected light signals in an example embodiment.

FIG. 9 is a series of schematic graph diagrams illustrating different output scenarios by keeping a constant gain of about 10 times and varying the amplitude differences of detected light signals. At part (i), a detected signal 902 at a detection assembly (compare 408 of FIG. 4) e.g. at point A of FIG. 4(a) undergoes signal conditioning provided by a circuit substantially similar to that of FIG. 4 and provides an output 904 at a non-inverting summing amplifier module (compare 416 of FIG. 4). As the amplitude difference at signal 902 is negligible e.g. about 25 mv, the output 904 with a gain of 10 times shows a suitable wave form within the saturation levels. The inventors recognise that the output 904 is a desirable output for measurement purposes. At part (ii), a detected signal 906 at the detection assembly undergoes signal conditioning provided by the circuit and provides an output 908 at the non-inverting summing amplifier module. As the amplitude difference at signal 906 is maintained to about 100 mv, the output 908 with a gain of about 10 times shows a suitable waveform and below saturation levels.

At part (iii), a detected signal 910 at the detection assembly undergoes signal conditioning provided by the circuit and provides an output 912 at the non-inverting summing amplifier module. As the amplitude difference of the detected signal 910 is about 400 mV, the output 912 with a gain of about 10 times shows a waveform with the amplitude on the top (see 914) reaching saturation. The top of the waveform corresponds to red AC signals.

At part (iv), a detected signal 916 at the detection assembly undergoes signal conditioning provided by the circuit and provides an output 918 at the non-inverting summing amplifier module. As the amplitude difference of the detected signal 918 is about 300 mV, the output 916 with a gain of about 10 times shows a waveform with the amplitude on the bottom (see 920) reaching saturation. The bottom of the waveform corresponds to IR AC signals.

Hence, even with a fixed gain of e.g. about 10 times, the inventors have recognised that the DC components of both the Red and IR light sources can be set to be as close as possible to each other so as to achieve a conditioned signal. The above may be achieved by tuning the illumination intensities of the light sources. In addition, a high gain can then be imposed without saturating the output signal, for a single path processing circuitry with toggling capabilities that can cater for low perfusion scenarios.

Thus, there can be provided an optical measurement device that allows a gain to be selected for obtaining AC components of a PPG signal. The optical measurement device can further control illumination intensities of light sources of an illumination assembly of the measurement device. The selectable gain and the control of the illumination intensities are used such that an output signal at the optical measurement device is within a predetermined voltage/amplitude range. The predetermined voltage/amplitude range is selected based on a known saturation level of the device.

In an example embodiment, to detect a low perfusion scenario, the inventors have recognised that a lower LED intensity for both the Red and IR light sources is preferred. Lowering the intensity of both the Red and IR light sources can allow for signals of a better quality, i.e. a larger amplitude. For example, a normal measurement uses about 14-16 mA and about 10-12 mA of driving current for the Red and IR light sources' intensity to reach a 2.5V DC value at the detector/detection assembly. A person with low perfusion uses about 10-12 mA and about 6-8 mA of driving current for the Red and IR light sources' intensity to reach a similar 2.5V DC value at the detector/detection assembly. Thus, if the detected level is more than 2.5V DC, the circuitry is able to determine that the situation is a low perfusion scenario. The circuitry is able to tune/track the intensity setting and thus, select the appropriate gain.

In an example embodiment, there is a further super low perfusion scenario, where even with the above approach, it is determined that the obtained AC signal is too small to identify the respective peaks of the signal. In other words, the maximum and minimum points of the AC signal cannot be accurately obtained. In such a case, the gain is increased to about 30 times.

Thus, in the example embodiment, there is a first process to determine if the scenario is a cold finger scenario, wherein lowering the intensity of both the Red and IR sources can allow for signals of a better quality or larger amplitude of e.g. 2.5V. Next, a selection is made between the gain settings of e.g. 20 or 30. As described above, if it is determined that the obtained AC signal is too small to effectively identify the maximum and minimum points of the AC signal, then the higher gain setting of e.g. 30 is chosen.

Thus, in the above described example embodiments, a signal processing circuitry can be provided that comprises a photodetector coupled with a transimpedance amplifier, a high-pass filter, a voltage follower module, an non-inverting amplifier with selectable gain and a non-inverting summing amplifier with unity gain. The circuitry can provide feedback using a microcontroller to intensity controls of one or more light sources. The circuitry can handle processing in a single path approach based on detection of light information relating to toggling of light sources. The circuitry can also handle low perfusion scenarios by selecting an appropriate gain and controlling intensities of light sources. In addition, the circuitry can allow effective measurement of low perfused human tissue conditions while maintaining a low power usage.

Therefore, in an example embodiment, an optical measurement device can be provided. The device can comprise an illumination assembly configured to output light to a surface portion of a user for measurement. The illumination assembly can comprise one or more light sources such as one or more LEDs. That is, the illumination can comprise a red light source and/or an infra-red light source. The device further comprises a detection assembly configured to detect the output light reflected from said surface portion of the user as a signal. The detection assembly can comprise a photodetector. The device can comprise an amplifier module directly or indirectly coupled to the detection assembly, the amplifier module configured to apply a gain to an alternating-current component of the detected signal. The device can further comprise a microcontroller coupled to the detection assembly and configured to assess a direct-current voltage level of the signal. The microcontroller is also configured to control the light output at the illumination assembly based on said assessing the direct-current voltage level. This can allow the microcontroller to determine whether there is a low perfusion scenario, and/or whether the illumination intensity of the illumination assembly is to be tuned, e.g. to move the amplitude difference formed based on a red and an IR light illumination to be closer together or e.g. whether the driving current of LEDs are to be reduced. In addition, the microcontroller is configured to select a gain value for said applying the gain based on said assessing the direct-current voltage level. For example, for a low perfusion scenario, a higher gain is selected.

In the example embodiment, the light sources are toggled on/off for the detection assembly to detect the reflected output light as a single signal. The processing or signal conditioning described can then be carried out in a single path processing approach. In the example embodiment, an amplitude difference between a maximum point and a minimum point of the single signal is maintained below a predetermined level by the microcontroller controlling the light output at the illumination assembly. In some example embodiments, the predetermined level can be about 100 mV. The predetermined level is obtained based on the alternating-current component of the signal being within a saturation level, upon the amplifier module applying the gain. Thus, for a gain of about 20 times in a coldfinger scenario, a difference of about 100 mV becomes about 2V, compared to a saturation voltage level of e.g. about 3.3V. It will be appreciated that within each signal, there is an inherent AC component and this may be e.g. 10 mV. Therefore, factoring a gain of 20 times, the amplified signals can have a span or a range of about 2.2V which is still within the 3.3V saturation range. This can ensure that the output from the circuitry is not saturated.

However, it will be appreciated that if the difference is about 200 mV, selecting a gain of 20 times due to a detected low perfusion condition can result in an output of about 4V, i.e. saturation of the circuit. In this regard, in catering for low perfusion using an adjustable gain at the AC signal processing path, the light sources can be tuned to output light power that are as close as possible, for detection by the detector, i.e. to provide a difference detected that is as small as possible.

In the example embodiment, a summing amplifier can be provided coupled to the amplifier module whereby the summing amplifier is configured to move the alternating-current component of the signal above a ground voltage level. This can provide advantages in digitising the processed signal. The saturation level is based on an output of the summing amplifier.

In the example embodiment, the microcontroller is configured to determine that a measurement is a low perfusion measurement based on said assessing the direct-current voltage level, and wherein if there is a low perfusion measurement, the microcontroller controls the light output at the illumination assembly to a lower intensity and selects a large gain value for said applying the gain. In such a scenario, the large gain value is about 20 to 30 times.

It is appreciated that the detected light information or Vppg signal e.g. to be transmitted to a personal mobile processing device for further processing has a substantial extent of ambient light interference. Therefore, ambient light or noise cancellation can be performed e.g. at the personal mobile processing device. The description below relating to ambient noise cancellation for SPO2 calculations can be implemented through software and/or hardware modules. The hardware modules can comprise electronic circuitry or dedicated application chips such as an ASIC chip. A graphical user interface (GUI) may be provided, such as an "app" or software application on a smartphone, to be run on the personal mobile processing device to implement and display the ambient noise cancellation.

To determine SpO2 values, for example, a proprietary lookup table is typically provided by manufacturers. A calculated ratio R is used for referring to the lookup table to determine SpO2 values.
R is defined as, $$R = \frac{\frac{AC_R}{DC_R}}{\frac{AC_{IR}}{DC_{IR}}}$$

where AC, DC refer to alternating current and direct current values respectively. The conditions IR and R refer to conditions whereby infra-red light and red light are used respectively. It is noted that ambient light noise is usually subtracted or removed in the R calculations.

In example embodiments, there can be provided a method and system for noise cancellation, e.g. for SpO2 measurements. In one example embodiment, AC and DC values are respectively obtained for a Red PPG signal measurement, an IR PPG signal measurement and an ambient PPG signal measurement (where both the red and IR LEDs are turned off). The maximum and minimum values of the PPG signal measurements are determined. A SpO2 value based on a ratio R value calculated using the determined maximum and minimum values can then be determined.

Advantageously, in the example embodiment, a signal reconstruction of true Red and/or IR PPG signals to remove ambient signal interference can be avoided. The inventors have recognised that by identifying and utilising only significant information for SpO2 calculation, an efficient and accurate calculation can be carried out. The inventors have recognized that by using only the maximum and minimum values of the respective red, IR and ambient signal pulses, the calculation of SpO2 can be carried out. For example, a maximum of the true Red PPG signal (devoid of ambient noise) can simply be obtained by subtracting the obtained maximum value of the Red PPG signal, obtained when the Red LED is turned on, with the obtained maximum value of the ambient PPG signal, i.e. when none of the LEDs is turned on.

In other words, instead of reconstructing a true Red PPG signal (devoid of ambient signal) and a true IR PPG signal (devoid of ambient signal), advantageously, reconstruction is avoided in example embodiments, and only the maximum and minimum values of 3 PPG signals are obtained for analysis to obtain SpO2 value. This can minimise processing and consume less power.

A feedback unit/personal processing device can be provided for removal of ambient noise signal from an optical measurement in an example embodiment. The device can comprise a coupling member e.g. for coupling to an optical measurement device. The coupling member can receive a first signal waveform obtained based on detecting light based on a first light illumination, a second signal waveform obtained based on detecting light based on a second light illumination, and a third signal waveform obtained based on detecting ambient light. The device can also comprise a processor module that can obtain respective maximum and minimum values of at least two of the first, second and third signal waveforms; and the processor can derive signal values of the first and second signal waveforms with the removal of ambient noise by using the maximum and minimum values of at least two of the first, second and third signal waveforms.

Figure 10:
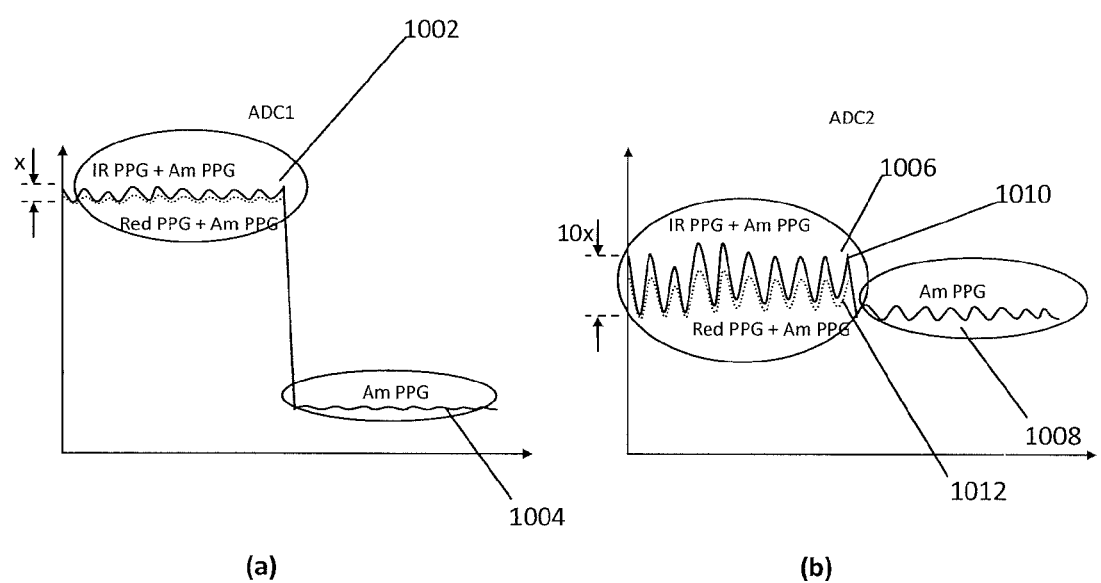
FIG. 10(a) is a graph schematically illustrating signals acquired at an analog to digital converter in an example embodiment.
FIG. 10(b) is a graph schematically illustrating alternating current (AC) signals acquired at an analog to digital converter in an example embodiment.

FIG. 10(a) is a graph illustrating signals acquired at an analog to digital converter (compare ADC1 of FIG. 4(a)) in an example embodiment. The y-axis is in terms of mV and the x-axis is in terms of ms. Numeral 1002 shows the signals obtained when the Red and IR LEDs are turned on during the toggling sequence 606 (FIG. 6(a)). Numeral 1004 shows the signals obtained when the Red and IR LEDs are turned off during the OFF condition 602 (FIG. 6(a)). As shown, the amplitude of the signals obtained during the toggling sequence 606 (FIG. 6) is notated as x'.

FIG. 10(b) is a graph illustrating AC signals acquired at an analog to digital converter (compare ADC2 of FIG. 4(a)) in an example embodiment. The y-axis is in terms of mV and the x-axis is in terms of ms. Numeral 1006 shows the AC signals when the Red and IR LEDs are turned on during the toggling sequence 606 (FIG. 6(a)). Numeral 1008 shows the AC signals when the Red and IR LEDs are turned off during the OFF condition 602 (FIG. 6(a)). The IR signals are shown with solid lines at 1010 and the Red signals are shown with dotted lines at 1012. With the amplification provided in FIG. 4(a), as shown, the difference between the Red and IR detected AC signals is notated as 10x', i.e. a gain of about 10 times has been provided.

The IR condition refers to when only the IR LED is turned on, while the Red condition refers to when only the Red LED is turned on. The IR and/or the Red conditions are illustrated in FIGS. 7(a) and 7(b). That is, even if the brief time period Δt 702 is included, the respective condition, Red or IR, is still relevant given the longer preceding amount of time when one of the LEDs is turned on. The ambient condition refers to when none of the LEDs are turned on, and the signal is obtained due to the ambient light conditions. See numeral 604 of FIG. 6(a).

With the AC and DC signal portions, the inventors have recognised that significant information can be further extracted for SpO2 calculation. Using the circuit of FIG. 4(a), it can be seen from FIGS. 10(a) and (b) that the AC and DC components of the Red and IR PPG signals are larger than those of the ambient PPG signal. Therefore, the contribution of the ambient PPG signal is less significant compared with the contribution of the RED or IR PPG signals. This can provide for a more accurate SpO2 calculation. That is, in example embodiments, the LED illumination intensity can be tuned to a level that provides for detected signals that provide as high a detected voltage as possible, without saturating the signals. The intensity can be controlled by the MCU. The tuning can ensure that both Red and IR signals transmitted to ADC1 can reach an amplitude level significantly higher than Ambient signals transmitted to ADC1. For example, if an Ambient signal at ADC1 is about 0.5V, both Red and IR signals at ADC1 can preferably be set at about 2V or above. This is described and illustrated in more detail below with FIG. 18. In addition, there can be steps taken to ensure that detected Ambient light signals are not too high. Exemplary steps are described and illustrated in more detail below with FIG. 17.

Based on the LED firing sequence as illustrated in FIG. 6, the data obtained at ADC1 and ADC2 can be processed to select the AC and DC components of the IR, Red and Ambient conditions.

The signals shown in FIGS. 10(a) and (b) can undergo further digital signal processing steps. The modules for such processing may not be all shown in FIG. 4. In the example embodiment, the DC data is passed through a low pass filter (e.g. filtering >0.8 Hz) and the AC data can be passed through a band pass filter (e.g. filtering <0.5 Hz and >20 Hz) (not shown in FIG. 4).

Figure 11:
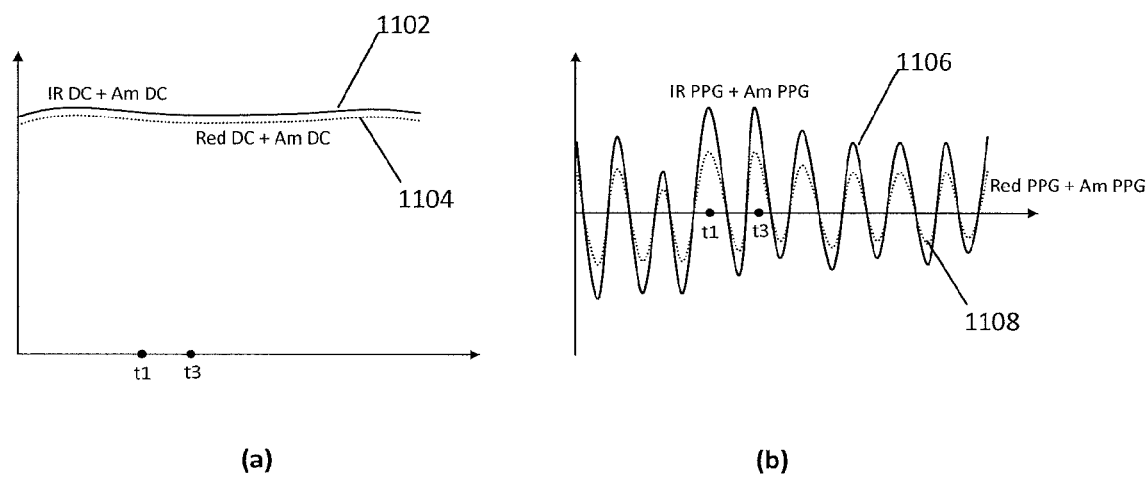
FIG. 11(a) is a graph schematically illustrating filtered DC signals in an example embodiment.
FIG. 11(b) is a graph schematically illustrating filtered AC signals in an example embodiment.

FIG. 11(a) is a graph illustrating filtered DC signals in an example embodiment. The y-axis is in terms of mV and the x-axis is in terms of ms. The graph shows filtered DC signals of when the Red and IR LEDs are turned on during the toggling sequence 606 (FIG. 6(a)). The IR signals are shown with solid lines at 1102 and the Red signals are shown with dotted lines at 1104.

FIG. 11(b) is a graph illustrating filtered AC signals in an example embodiment. The y-axis is in terms of mV and the x-axis is in terms of ms. The graph shows filtered AC signals of when the Red and IR LEDs are turned on during the toggling sequence 606 (FIG. 6(a)). The IR signals are shown with solid lines at 1106 and the Red signals are shown with dotted lines at 1108.

Figure 12:
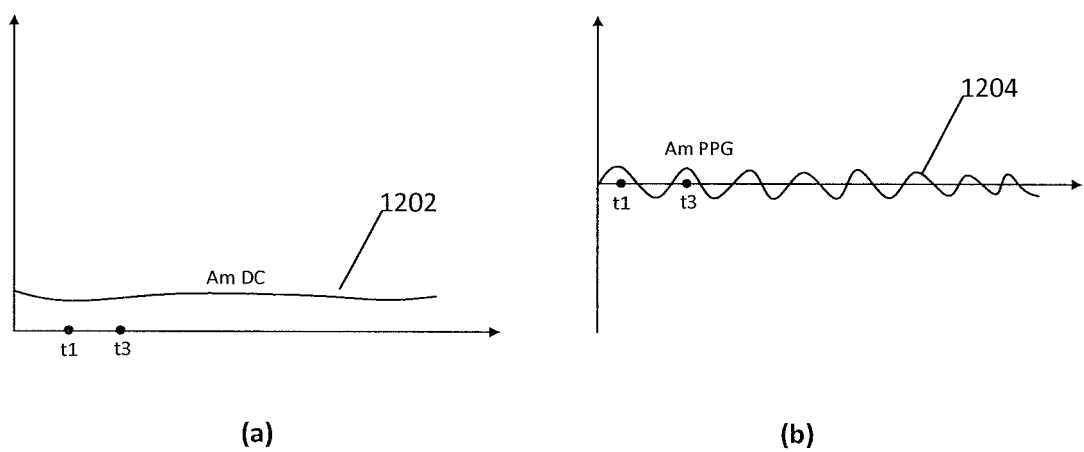
FIG. 12(a) is a graph schematically illustrating filtered DC signals for an ambient PPG signal in an example embodiment.
FIG. 12(b) is a graph schematically illustrating filtered AC signals for an ambient PPG signal in an example embodiment.

FIG. 12(a) is a graph illustrating filtered DC signals for an ambient PPG signal in an example embodiment. The y-axis is in terms of mV and the x-axis is in terms of ms. The graph shows filtered DC signals 1202 when the Red and IR LEDs are turned off during the OFF condition 602 (FIG. 6(a)).

FIG. 12(b) is a graph illustrating filtered AC signals for an ambient PPG signal in an example embodiment. The y-axis is in terms of mV and the x-axis is in terms of ms. The graph shows filtered AC signals 1204 when the Red and IR LEDs are turned off during the OFF condition 602 (FIG. 6(a)).

From FIGS. 11(b) and 12(b), the maximum and minimum points for each cycle, and the corresponding data and time for those maximum and minimum points are identified, see t1 and t3. It will be appreciated that the maximum and minimum values can be obtained using any peak detection techniques.

Figure 13:
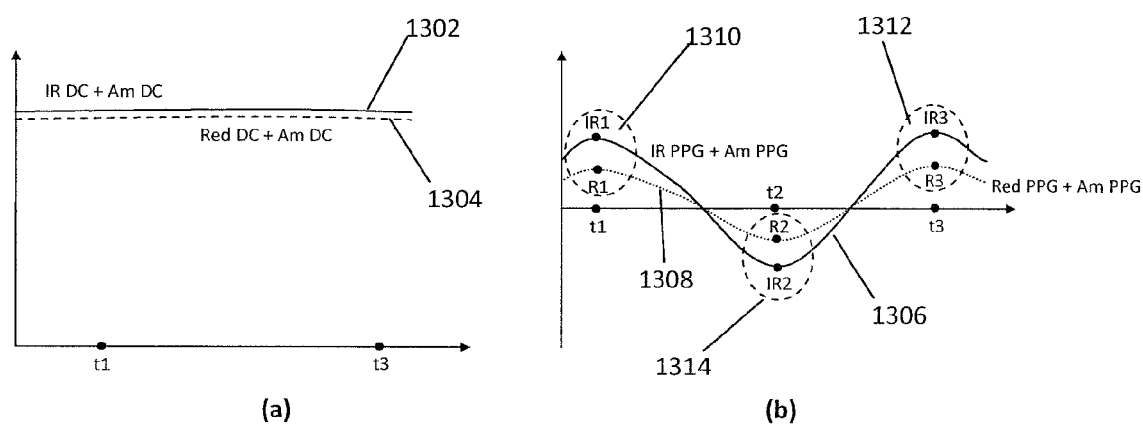
FIG. 13(a) is an enlarged version of FIG. 11(a).
FIG. 13(b) is an enlarged version of FIG. 11(b).

FIG. 13(a) is an enlarged version of FIG. 11(a), focusing on a specific period between $t_1$ to $t_3$ of the filtered DC signal. The IR signals are shown with solid lines at 1302 and the Red signals are shown with dotted lines at 1304.

FIG. 13(b) is an enlarged version of FIG. 11(b), focusing on a specific period between $t_1$ to $t_3$ of the filtered AC signal. The IR signals are shown with solid lines at 1306 and the Red signals are shown with dotted lines at 1308. The maximum point data at t1 and t3 are identified as IR1, R1, IR3, R3 accordingly. See numerals 1310, 1312 respectively. The minimum point data at t2 is identified as IR2, R2. See numeral 1314.

Figure 14:
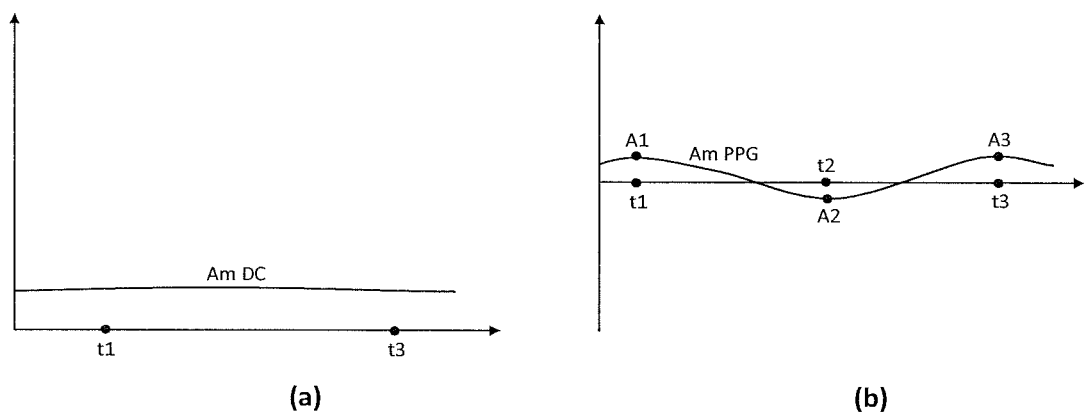
FIG. 14(a) is an enlarged version of FIG. 12(a).
FIG. 14(b) is an enlarged version of FIG. 12(b).

FIG. 14(a) is an enlarged version of FIG. 12(a) focusing on a specific period between t1 to t3 of the filtered DC signal.

FIG. 14(b) is an enlarged version of FIG. 12(b), focusing on a specific period between t1 to t3 of the filtered AC signal. The maximum point data at t1 and t3 are identified as A1, A3 accordingly. The minimum point data at t2 is identified as A2.

It should be noted that the notations such as t1, t2, t3 are arbitrary notations for signifying three timings and are not the same when referred to for an IR condition, a Red condition and an Ambient condition.

It will be appreciated that in an ideal situation, e.g. with individual photodetectors and signal paths for all 3 conditions (IR, Red and Ambient), and perfectly noise free conditions, all peaks and troughs may in theory occur at the same points. In other words, t1, t2 and t3 are the same when referring to the various conditions. In the present examples, because a single path is utilized, a peak sampled during the IR condition cannot be simultaneously measured for the R condition. As such, there are minor differences in peak and trough, e.g. t1, t2 and t3, times. If sampling is on a basis of IR, Red and Ambient conditions i.e. one sample per condition, it can be expected that the peaks and troughs of the respective signals (IR, R and Ambient), e.g. at t1, t2 and t3, may only be one sample off from each other. If the timings are too far off of each other (e.g. 2 or more samples apart), the particular set of samples can be rejected from the calculations if desired.

In the presently described example embodiments, as there are toggling and ambient phases (e.g. 606 and 602 of FIG. 6(a)), the ambient signal peaks and troughs cannot be obtained at the same time as the R and IR peaks and troughs. As such, individual signals for IR, R and ambient conditions are "reconstructed" and analysed separately. This can also be extended to a 3 phase sequence, e.g. IR condition on for 15 seconds, R condition on for 15 seconds and ambient condition on for 15 seconds.

With the information from FIGS. 13(a), 13(b), 14(a) and 14(b), a ratio R can be calculated by the following:

$$DC_{IR} + DC_{Am} = \frac{\sum_{t3}^{t1} DC_{IR+Am}}{n_{t1-t3}} \times \text{Gain}$$

$$AC_{IR} + AC_{Am} = \frac{(IR1 + IR3)}{2} - IR2$$

$$DC_R + DC_{Am} = \frac{\sum_{t3}^{t1} DC_{R+Am}}{n_{t1-t3}} \times \text{Gain}$$

$$AC_R + AC_{Am} = \frac{(R1 + R3)}{2} - R2$$

$$DC_{Avg,Am} = \frac{\sum_{i_{cycle}} \left( \frac{\sum_{t3}^{t1} DC_{Am}}{n_{t1-t3}} \right)}{i_{cycle}} \times \text{Gain}$$

$$AC_{Avg,Am} = \frac{\sum_{i_{cycle}} \left( \frac{(A1+A3)}{2} - A2 \right)}{i_{cycle}}$$

where $DC_{IR}+DC_{Am}$ is the DC value of one cycle of the IR LED being turned on during the toggle sequence 606 (FIG. 6); $n_{t1-t3}$ is the number of sampling points within the t1 to t3 time frame, i.e. an average of the values is being obtained (for DC measurements); $AC_{IR}+AC_{Am}$ is the AC value of one cycle of the IR LED being turned on during the toggle sequence 606 (FIG. 6); $DC_R+DC_{Am}$ is the DC value of one cycle of the Red LED being turned on during the toggle sequence 606 (FIG. 6); $AC_R+AC_{Am}$ is the AC value of one cycle of the Red LED being turned on during the toggle sequence 606 (FIG. 6); $DC_{avg,Am}$ is the average DC value of the ambient signal detected during the OFF condition 602 (FIG. 6); $i_{cycle}$ is the number of cycles taken for analysis and $AC_{avg,Am}$ is AC the average AC value of the ambient signal detected during the OFF condition 602 (FIG. 6). The gain is set to be the same when both LEDs are turned ON. Therefore, during calculations, the gain value cancels out and therefore can be set as any arbitrary value.

The inventors have recognised that the relationship between light intensity (I) and amplitude (A) is as follows:

$$I \alpha A^2$$

$$I = kA^2$$

Hence, $$I_{signal} = I_{signal+am} - I_{am}$$

$$kA_{signal}^2 = kA_{signal+am}^2 - kA_{am}^2$$

$$A_{signal} = \sqrt{A_{signal+am}^2 - A_{am}^2}$$

Therefore, using the intensity to amplitude relationship above, where $A_{am}^2$ is substituted with $DC_{Avg,Am}^2$, and the $A_{signal+am}^2$ is respectively substituted with the square of average values over an $i_{cycle}$ of the respectively DC or AC calculations from the set of equations above.

$$DC_{IR} = \sqrt{\left( \frac{\sum_{i_{cycle}} (DC_{IR} + DC_{Am})}{i_{cycle}} \right)^2 - DC_{Avg,Am}^2}$$

$$AC_{IR} = \sqrt{\left( \frac{\sum_{i_{cycle}} (AC_{IR} + AC_{Am})}{i_{cycle}} \right)^2 - AC_{Avg,Am}^2}$$

$$DC_R = \sqrt{\left( \frac{\sum_{i_{cycle}} (DC_R + DC_{Am})}{i_{cycle}} \right)^2 - DC_{Avg,Am}^2}$$

$$AC_R = \sqrt{\left( \frac{\sum_{i_{cycle}} (AC_R + AC_{Am})}{i_{cycle}} \right)^2 - AC_{Avg,Am}^2}$$

Typically, $$R = \frac{\frac{AC_R}{DC_R}}{\frac{AC_{IR}}{DC_{IR}}}$$

Thus, in the above described example embodiment, direct-current (DC) and alternating-current (AC) values of a first (e.g. red), second (e.g. IR) and third (e.g. ambient) signal waveforms can be obtained based on the respective maximum and minimum values. The DC and AC values of the third signal waveform can be average values obtained over a plurality of cycles and based on the maximum and minimum values of the third signal waveform. The ratio R can be determined based on using the DC and AC values of the first and second waveforms and the average values obtained from the third signal waveform; and wherein the ratio R is usable for referencing a lookup table.

With the ratio R, SpO2 or the saturation of hemoglobin with oxygen (in blood) can be determined. That is, in some examples, the ratio R can be used to refer to a proprietary lookup table provided by a manufacturer to determine the corresponding SpO2 value. The lookup table can be stored in a database that is in turn loaded onto the personal mobile processing device and the lookup operation is automated.

In example embodiments, optionally, it is possible to determine the quality of the signals so as to inform the user on the accuracy of, for example, a SpO2 measurement.

The quality of a signal can be measured by a propagation error which takes in account the deviation of the 6 parameters used in the calculation of R. i.e.

$$R = f(AC_{ir}, AC_r, AC_{am}, DC_{ir}, DC_r, DC_{am})$$

The inventors have recognised that, indirectly, deviation σR reflects the confidence level of the computation result of R. The calculated propagation error may be displayed on a screen of a personal mobile processing device to inform the user of the potential accuracy of the SpO2 measurement.

Alternatively, instead of the calculated propagation error, a representative description of the propagation error may be displayed. For example, for a propagation error of more than e.g. 30% of the mean of the calculated R, the user may be informed that the measured SpO2 is highly inaccurate and may be advised to retake the readings at a more suitable location. As another example, for a deduced propagation error of less than e.g. 10%, the user may be informed that the measured SpO2 is relatively accurate.

The equations below illustrate the algorithm for determining the accuracy.

$$R = f(AC_{ir}, AC_r, AC_{am}, DC_{ir}, DC_r, DC_{am})$$

$$\sigma_R^2 = \left(\frac{\partial R}{\partial AC_{ir}}\right) \cdot \sigma_{AC_{ir}}^2 + \left(\frac{\partial R}{\partial AC_r}\right) \cdot \sigma_{AC_r}^2 + \left(\frac{\partial R}{\partial AC_{am}}\right) \cdot \sigma_{AC_{am}}^2 +$$
$$\left(\frac{\partial R}{\partial DC_{ir}}\right) \cdot \sigma_{DC_{ir}}^2 + \left(\frac{\partial R}{\partial DC_r}\right) \cdot \sigma_{DC_r}^2 + \left(\frac{\partial R}{\partial DC_{am}}\right) \cdot \sigma_{DC_{amr}}^2$$

Further, each parameter has individual deviation as follows, $$DC_{ir} = DC_{avg,ir} + \sigma_{DC_{ir}} \quad AC_{ir} = AC_{avg,ir} + \sigma_{AC_{ir}}$$

$$DC_r = DC_{avg,r} + \sigma_{DC_r} \quad AC_r = AC_{avg,r} + \sigma_{AC_r}$$

$$DC_{am} = DC_{avg,am} + \sigma_{DC_{amr}} \quad AC_{am} = AC_{avg,am} + \sigma_{AC_{amr}}$$

Hence, the average value of R $$R_{avg} = \sqrt{\left[\frac{AC_{avg,r}^2 - AC_{avg,am}^2}{DC_{avg,r}^2 - DC_{avg,am}^2}\right] \times \left[\frac{DC_{avg,ir}^2 - DC_{avg,am}^2}{AC_{avg,ir}^2 - AC_{avg,am}^2}\right]}$$

$$\sigma_R =$$

$$R_{avg} \times \sqrt{\begin{array}{c} \frac{\sigma_{AC_{ir}}^2}{(AC_{avg,ir} - AC_{avg,am})^2} + \frac{\sigma_{DC_{ir}}^2}{(DC_{avg,ir} - DC_{avg,am})^2} + \\ \frac{\sigma_{AC_r}^2}{(AC_{avg,r} - AC_{avg,am})^2} + \frac{\sigma_{DC_r}^2}{(DC_{avg,r} - DC_{avg,am})^2} + \\ \frac{[(AC_{avg,ir} - AC_{avg,am}) - (AC_{avg,r} - AC_{avg,am})]^2 [\sigma_{AC_{am}}^2]}{(AC_{avg,ir} - AC_{avg,am})^2 (AC_{avg,r} - AC_{avg,am})^2} + \\ \frac{[(DC_{avg,r} - DC_{avg,am}) - (DC_{avg,ir} - DC_{avg,am})]^2 [\sigma_{DC_{am}}^2]}{(DC_{avg,r} - DC_{avg,am})^2 (DC_{avg,ir} - DC_{avg,am})^2} \end{array}}$$

Therefore, it can be derived that $$R = R_{avg} \pm \sigma_R$$

In another example embodiment, the ratio R can be determined using averages of maximum and minimum values. In the example embodiment, each Red and IR PPG signal are paired on a per cycle basis. A subtraction is carried out using an average ambient signal value. The average ambient signal value can be obtained before or after obtaining the Red and IR PPG signals.

Figure 15:
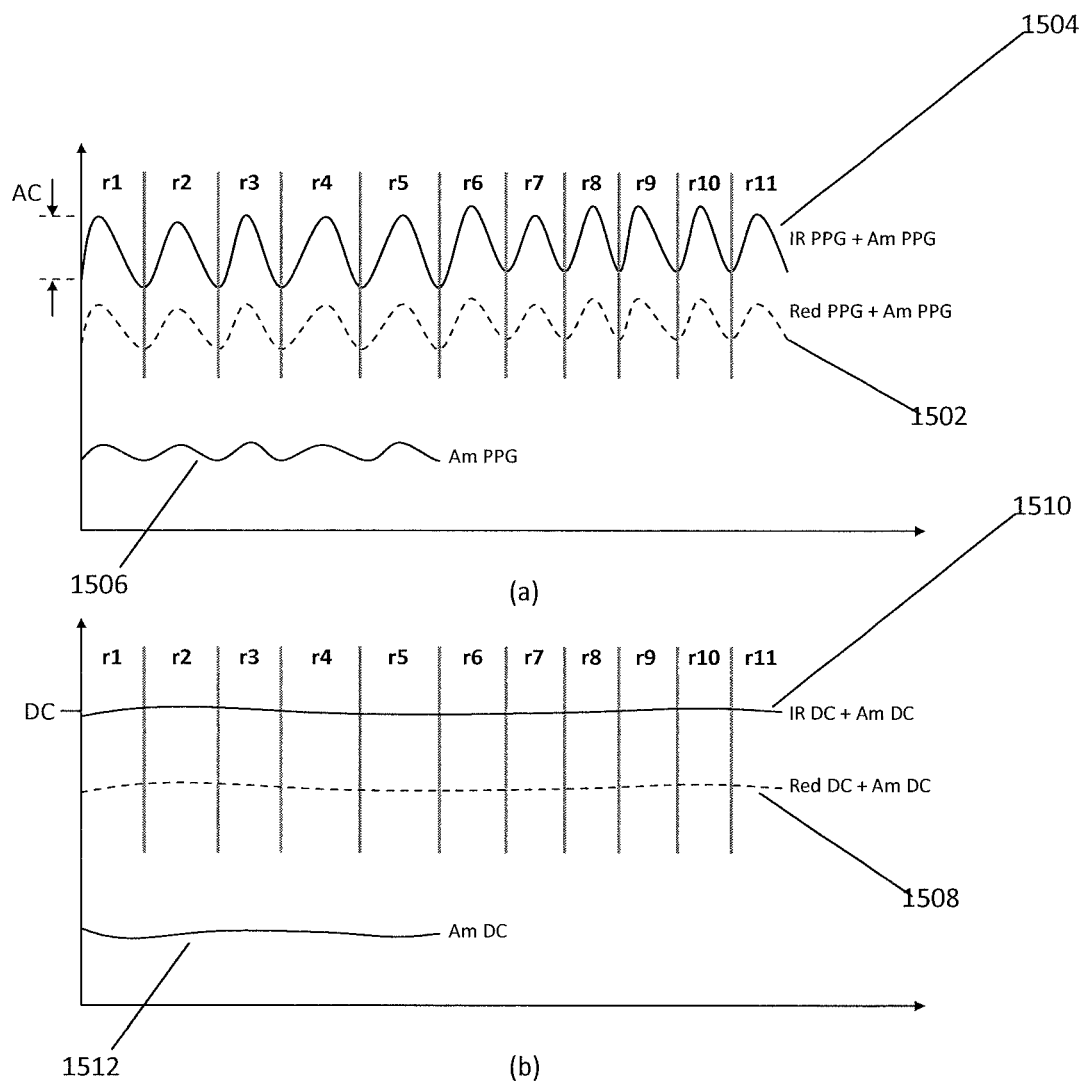
FIG. 15 is a schematic graph illustrating PPG signals obtained for a plurality of cycles in an example embodiment.

FIG. 15(a) is a schematic graph illustrating PPG AC signals obtained for a plurality of cycles in an example embodiment. FIG. 15(b) is a schematic graph illustrating PPG DC signals obtained for a plurality of cycles in an example embodiment. As illustrated as an example, there are 11 cycles shown in FIGS. 15(a) and (b). The Red PPG AC signals over the cycles are shown at numeral 1502, the IR PPG AC signals over the cycles are shown at numeral 1504, and the ambient PPG AC signals are shown at numeral 1506. In FIGS. 15(a) and (b), 11 cycles of IR and RED PPG signals and 5 cycles of ambient PPG signals are shown. This is because the period for obtaining the ambient PPG signals i.e. the ambient phase, is shorter than the toggling phase. It will be appreciated that any number of cycles for each of the signals (Red, IR or ambient) may be used. The Red PPG DC signals over the cycles are shown at numeral 1508, the IR PPG DC signals over the cycles are shown at numeral 1510, and the ambient PPG DC signals are shown at numeral 1512. The ambient PPG DC and AC signals are used to obtain an average ambient signal value $avgDC_{am}$ and $avgAC_{am}$ respectively. In the example embodiment implementing a single path system, the ambient sampling (compare 602) is performed after/before the toggling phase. Therefore, the Ambient signals shown in FIGS. 15(a) and (b) have been time shifted to show aligned cycles with the Red and IR signals, even though they are not necessarily aligned in real time.

A plurality of R values are obtained as follows:

$$R_1 = \frac{R_{r1}}{R_{ir1}} = \sqrt{\frac{(AC_{r1}^2 - avgAC_{am}^2)}{(DC_{r1}^2 - avgDC_{am}^2)} \times \frac{(DC_{ir1}^2 - avgDC_{am}^2)}{(AC_{ir1}^2 - avgAC_{am}^2)}} \rightarrow \text{Cycle 1}$$

$$R_2 = \frac{R_{r2}}{R_{ir2}} = \sqrt{\frac{(AC_{r2}^2 - avgAC_{am}^2)}{(DC_{r2}^2 - avgDC_{am}^2)} \times \frac{(DC_{ir2}^2 - avgDC_{am}^2)}{(AC_{ir2}^2 - avgAC_{am}^2)}} \rightarrow \text{Cycle 2}$$

↓

↓

$$R_n = \frac{R_{r_n}}{R_{ir_n}} = \sqrt{\frac{(AC_{r_n}^2 - avgAC_{am}^2)}{(DC_{r_n}^2 - avgDC_{am}^2)} \times \frac{(DC_{ir_n}^2 - avgDC_{am}^2)}{(AC_{ir_n}^2 - avgAC_{am}^2)}} \rightarrow \text{Cycle } n$$

Therefore, $$R_{avg} = \frac{\sum (R_1 + R_2 + \ldots + R_n)}{n}$$

Thus, for the above described example embodiment, direct-current (DC) and alternating-current (AC) values of at least two of the first (e.g. red), second (e.g. IR) and third (e.g. ambient) signal waveforms can be obtained based on the respective maximum and minimum values obtained in one/each cycle. The DC and AC values of the third signal waveform are average values obtained over a plurality of cycles e.g. 11 cycles described above. A ratio R for each cycle (e.g. $R_1$, $R_2$ etc.) can be obtained based on using the DC and AC values of the first and the second signal waveforms and the average values obtained from the third signal waveform. An average R value (e.g. $R_{avg}$) can be obtained based on using the ratio R for a plurality of cycles (e.g. $R_1$, $R_2$ etc.); and wherein the R value (e.g. $R_{avg}$) is usable for referencing a lookup table.

For the calculation of signal quality, the following equation is used.

$$\sigma = \sqrt{\frac{\sum_{i=1}^{n}(R_i - R_{avg})^2}{n}}$$

Therefore, in the above example embodiments for obtaining R, only significant information for SpO2 determination is extracted. This can advantageously reduce circuitry cost, optimise space and minimise power consumption.

Figure 16:
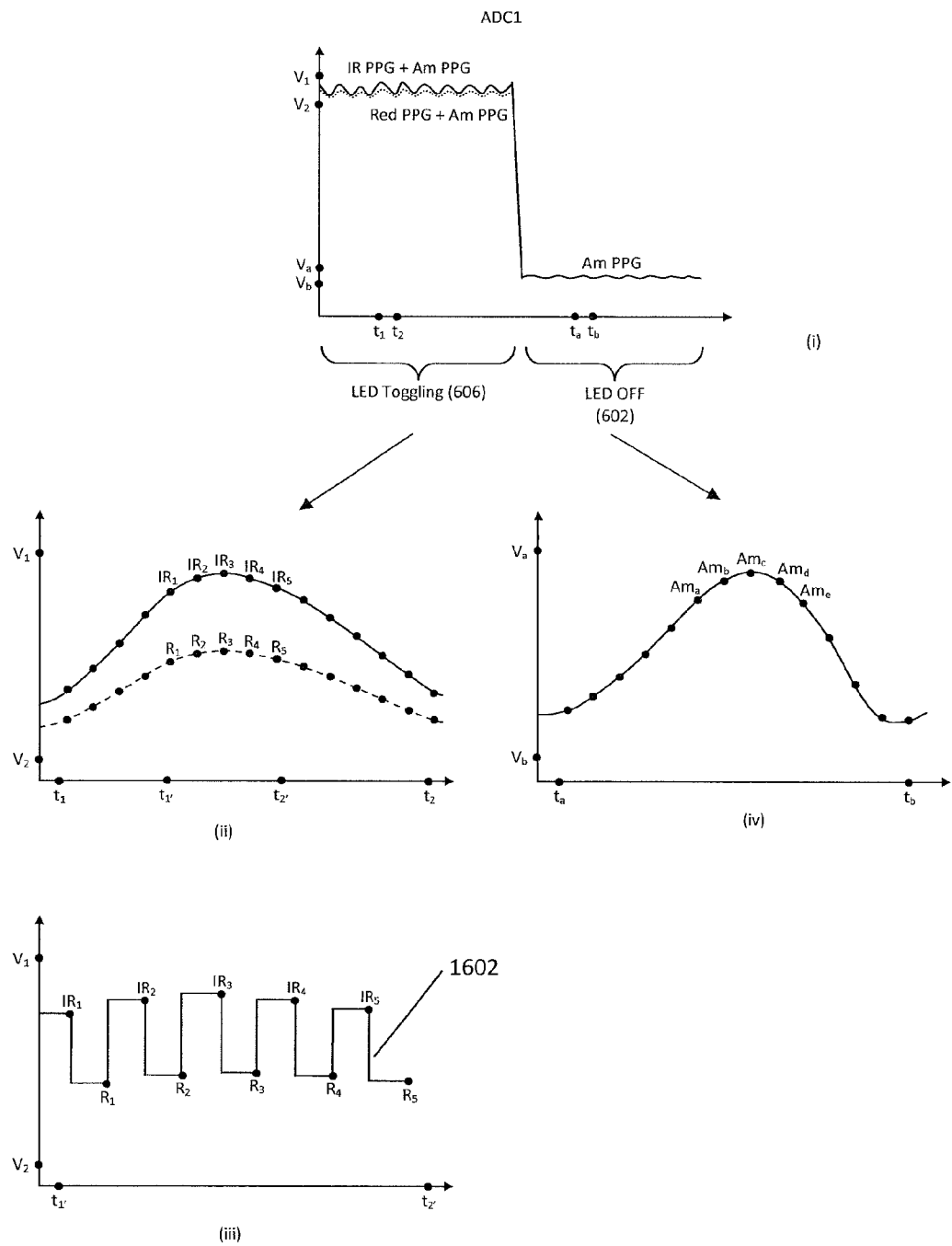
FIG. 16 shows how a signal forms at an analog to digital converter when two LEDs toggle and when both LEDs are switched off in an example embodiment.

FIG. 16 shows how a signal forms at an analog to digital converter (compare ADC1 422 of FIG. 4) when two LEDs toggle and when both LEDs are switched off in an example embodiment. During toggling, the signal detected at a photodetector PD is shown in part (iii) of FIG. 16. The square wave 1602 is the detected signal which reflects the sampled points based on the toggling timing sequence. At each sampled point of Red ($R_1, R_2 \ldots R_n$,) and IR ($IR_1, IR_2, \ldots IR_n$), analog to digital conversion ADC is executed and the values captured by a microcontroller MCU. Data is separated or de-multiplexed in the MCU and can be presented as individual Red and IR data (or separated Red and IR PPG signals) in dots format, as shown in part (ii) of FIG. 16. Over a larger time frame, a PPG signal comprising Red and IR are formed, as shown in part (i) of FIG. 16. When both LEDs are switched off, only 1 signal (Ambient) is present and thus the ADC captured values are not separated. This signal at part (i) passes through the signal conditioning and produces a signal substantially similar to FIG. 10(b).

Figure 17:
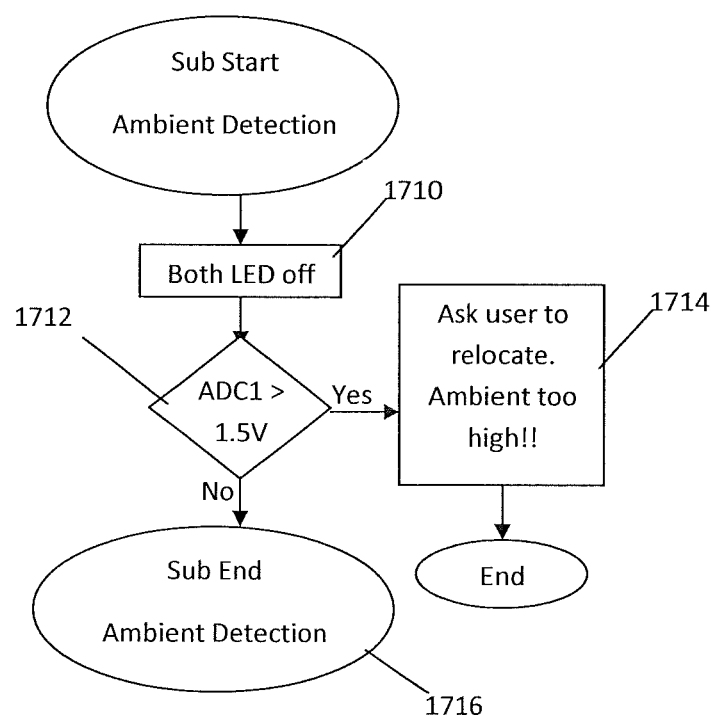
FIG. 17 is a schematic flow diagram illustrating an ambient light detection process in an example embodiment.

FIG. 17 is a schematic flow diagram illustrating an ambient light detection process in an example embodiment. An optical measurement device is coupled to a personal mobile processing device. At step 1710, both the Red and IR LEDs are switched off. At step 1712, it is determined whether ADC1 of the MCU of the measurement device reads a value of e.g. more than about 1.5V. If the reading is more than the exemplary value of 1.5V at step 1712, at step 1714, the personal mobile processing device is configured to alert the user to relocate to another location for the optical measurement as the ambient light interference is determined to be too high. If the reading is less than the exemplary value of 1.5V at step 1712, at step 1716, the ambient light detection process ends.

Figure 18:
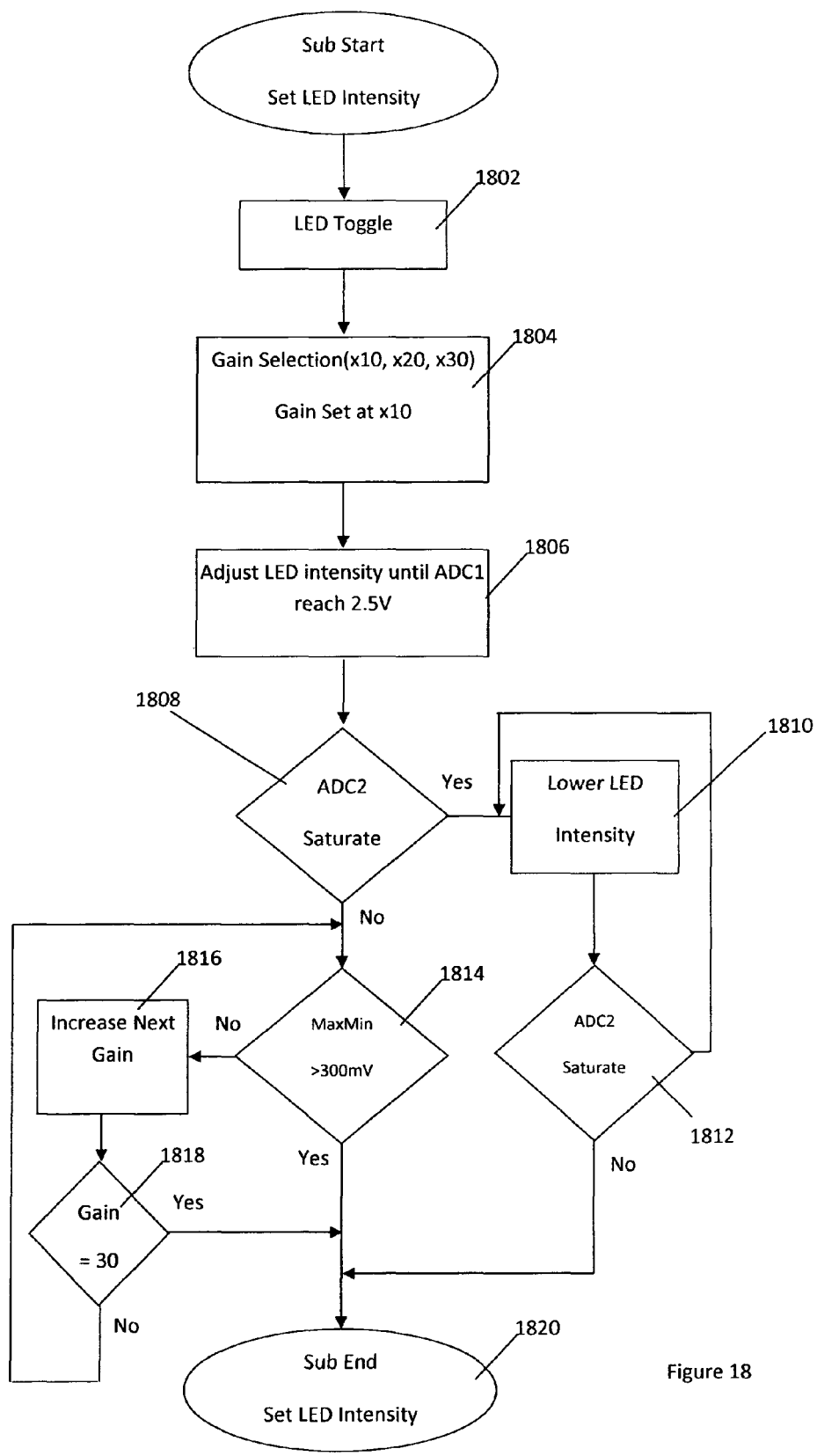
FIG. 18 is a schematic flow diagram illustrating a light intensity setting process in an example embodiment.

FIG. 18 is a schematic flow diagram illustrating a light intensity setting process in an example embodiment. This process can be used for scenarios for normal measurements. At step 1802, a LED toggle sequence is performed. At step 1804, the light data detected at step 1802 undergoes a gain process. The gain may be selected from, for example, ten times, twenty times or thirty times etc. In the example embodiment, a gain of e.g. ten times is selected. At step 1806, it is determined whether ADC1 of the MCU of the measurement device reads a value of e.g. about 2.5V. The LEDs intensity is adjusted until the reading reaches 2.5V. This can ensure that the contribution of the ambient light is not substantially more than the contribution of the LEDs, when measured by the detector. In this example embodiment, because the ambient light cannot exceed 1.5V, and each LED is adjusted to result in a measurement of about 2.5V, the ambient light does not exceed more than about 60% of the light detected by the detector, when each LED is switched on. At step 1808, it is determined whether ADC2 of the MCU of the measurement device reaches saturation, e.g. at about 3.3V. If ADC2 has reached saturation, at step 1810, the LEDs intensity is lowered until ADC2 is no longer saturated at step 1812.

If ADC2 has not reached saturation at step 1808, at step 1814, it is determined whether the maximum and minimum data points have a difference of more than e.g. about 300 mV.

If the difference at step 1814 is not more than e.g. about 300 mV, at step 1816, the gain can be increased. At step 1818, it is determined whether the gain is thirty times. If the gain is thirty times, the LED intensity is set and the setting process is ended at step 1820. If the gain is not yet thirty times at step 1818, the process loops back to step 1814.

Figure 19:
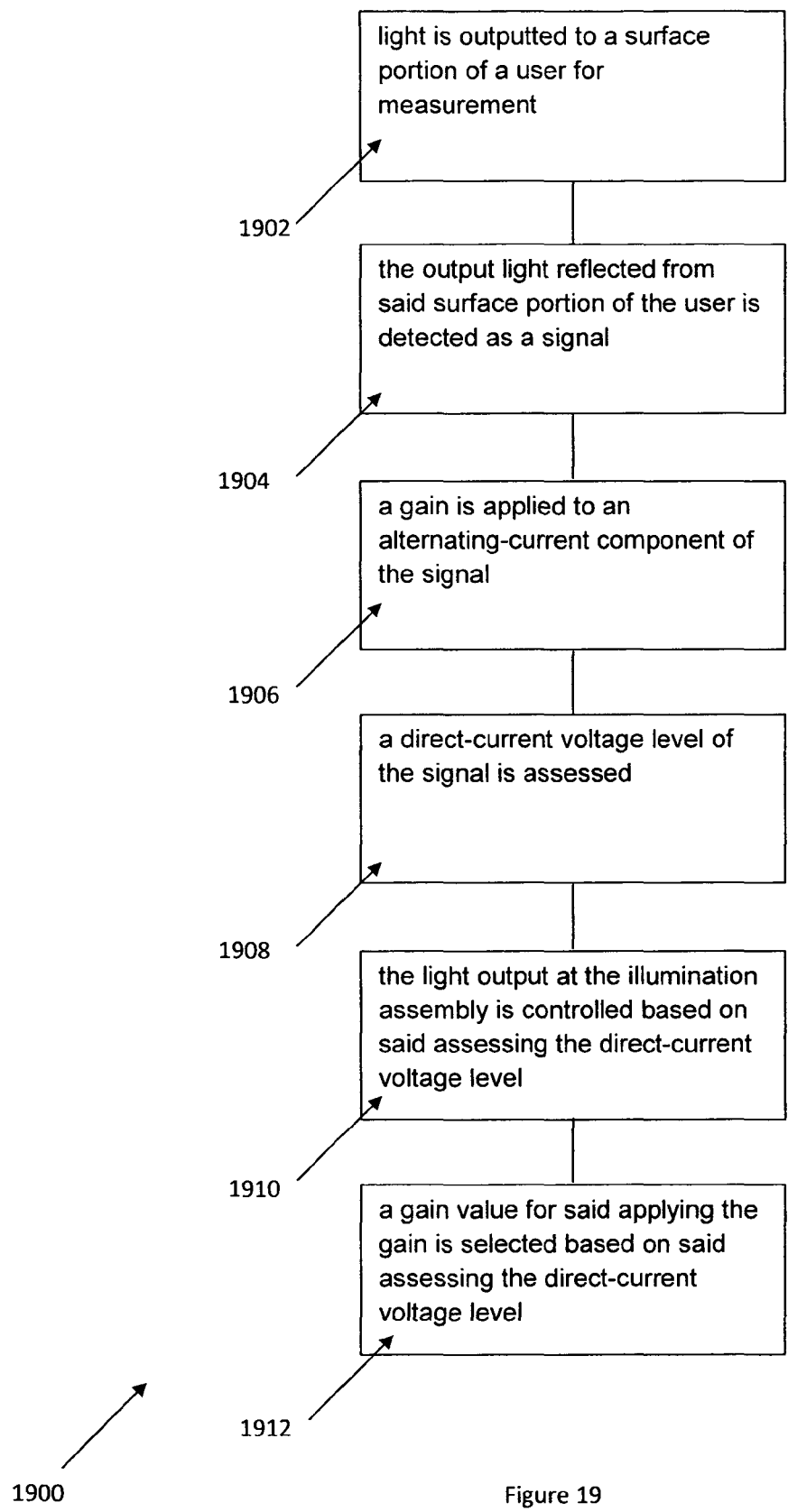
FIG. 19 is a schematic flowchart for illustrating a method for optical measurement in an example embodiment.

FIG. 19 is a schematic flowchart 1900 for illustrating a method for optical measurement in an example embodiment. At step 1902, light is outputted to a surface portion of a user for measurement. At step 1904, the output light reflected from said surface portion of the user is detected as a signal. At step 1906, a gain is applied to an alternating-current component of the signal. At step 1908, a direct-current voltage level of the signal is assessed. At step 1910, the light output at the illumination assembly is controlled based on said assessing the direct-current voltage level. At step 1912, a gain value for said applying the gain is selected based on said assessing the direct-current voltage level.

Figure 20:
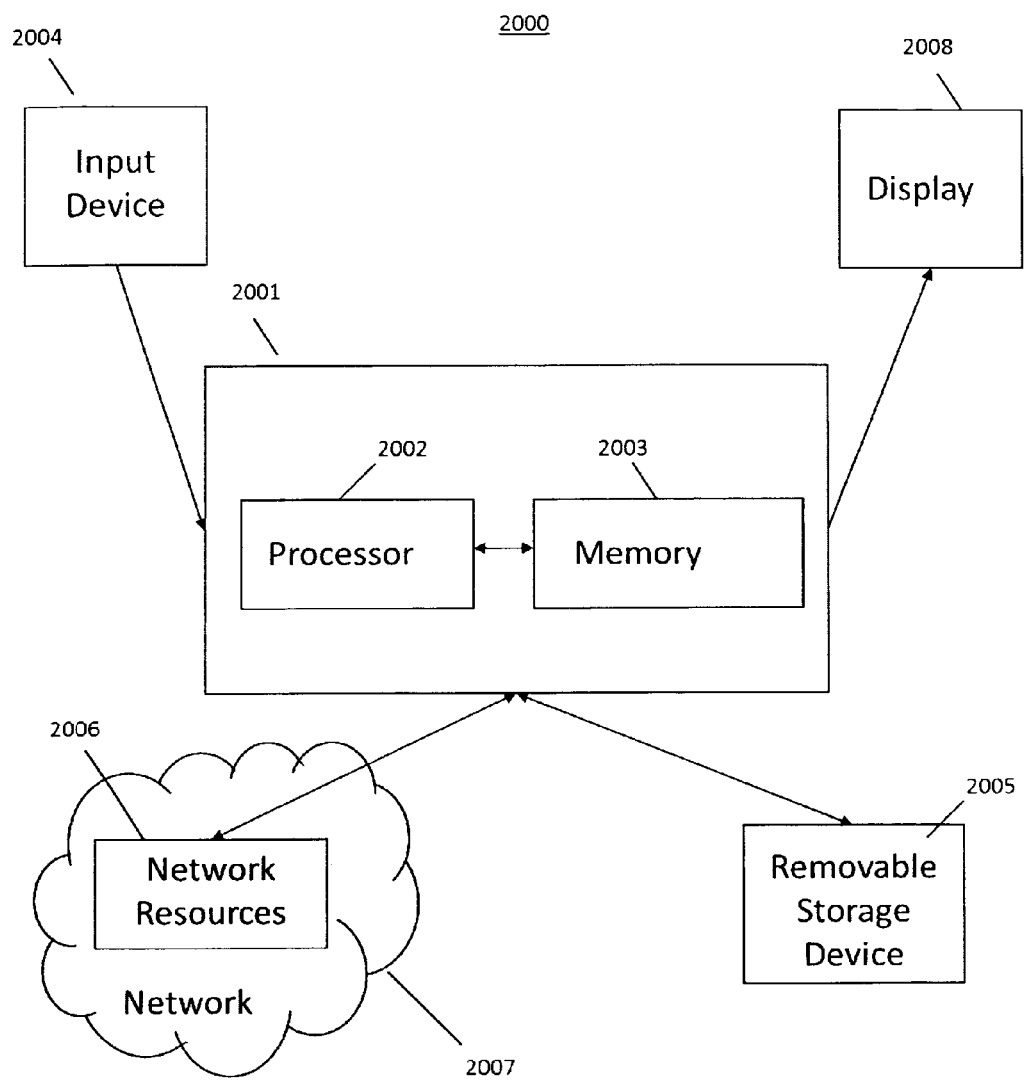
FIG. 20 is a block diagram schematically illustrating an embodiment of a computer/server system suitable for implementing an example embodiment.

FIG. 20 is a block diagram that illustrates an embodiment of a computer/server system 2000 upon which an embodiment of the inventive methodology may be implemented. The system 2000 includes a computer/server platform 2001 including a processor 2002 and memory 2003 which operate to execute instructions, as known to one of skill in the art. The term "computer-readable medium" as used herein refers to any medium that participates in providing instructions to processor 2002 for execution. Additionally, the computer platform 2001 receives input from a plurality of input devices 2004, such as a keyboard, mouse, touch device or verbal command. The computer platform 2001 may additionally be connected to a removable storage device 2005, such as a portable hard drive, optical media (CD or DVD), disk media or any other medium from which a computer can read executable code. The computer platform may further be connected to network resources 2006 which connect to the Internet or other components of a local public or private network. The network resources 2006 may provide instructions and data to the computer platform from a remote location on a network 2007. The connections to the network resources 2006 may be via wireless protocols, such as the 802.11 standards, Bluetooth® or cellular protocols, or via physical transmission media, such as cables or fiber optics. The network resources may include storage devices for storing data and executable instructions at a location separate from the computer platform 2001. The computer interacts with a display 2008 to output data and other information to a user, as well as to request additional instructions and input from the user. The display 2008 may therefore further act as an input device 2004 for interacting with a user.

It will be appreciated by a person skilled in the art that other variations and/or modifications may be made to the specific embodiments without departing from the spirit or scope of the invention as broadly described. The present embodiments are, therefore, to be considered in all respects to be illustrative and not restrictive.

The invention claimed is:

1. An optical measurement (OM) device, the device comprising:
    an illumination assembly configured to output light from two or more light sources to a surface portion of a user for measurement;
    a detection assembly configured to detect the output light from the two or more light sources reflected from said surface portion of the user as a signal;
    an amplifier module coupled to the detection assembly configured to apply a gain to an alternating-current component of the signal; and a microcontroller coupled to the detection assembly configured to assess a direct-current voltage level of the signal, wherein the microcontroller is configured to control the light output at the illumination assembly based on said assessing the direct-current voltage level such that the alternating-current component of the signal is within a saturation level, upon the amplifier module applying the gain, and wherein the microcontroller is configured to select a gain value for said applying the gain based on said assessing the direct-current voltage level.

2. The OM device of claim 1, wherein the microcontroller is configured to determine that a measurement is a low perfusion measurement based on said assessing the direct-current voltage level, and wherein if there is a low perfusion measurement, the microcontroller controls the light output at the illumination assembly to a lower intensity than that producing the present direct-current voltage level and selects a large gain value as compared to normal measurements for said applying the gain.

3. The OM device of claim 2, wherein the large gain value is about 20 to 30 times.

4. The OM device of claim 1, wherein the illumination assembly comprises a red light source and/or an infra-red light source.

5. The OM device of claim 4, wherein the light sources are toggled on/off for the detection assembly to detect the reflected output light as a single signal.

6. The OM device of claim 5, wherein an amplitude difference between a maximum point and a minimum point of the single signal is maintained below a predetermined level by the microcontroller controlling the light output at the illumination assembly.

7. The OM device of claim 6, wherein the predetermined level is obtained based on the alternating-current component of the signal being within the saturation level, upon the amplifier module applying the gain.

8. The OM device of claim 7, further comprising a summing amplifier coupled to the amplifier module, the summing amplifier configured to move the alternating-current component of the signal above a ground voltage level.

9. The OM device of claim 8, wherein the saturation level is based on an output of the summing amplifier.

10. A method for optical measurement, the method comprising:
outputting light from two or more light sources to a surface portion of a user for measurement;
detecting the output light from the two or more light sources reflected from said surface portion of the user as a signal;
assessing a direct-current voltage level of the signal;
controlling the light output at the illumination assembly based on said assessing the direct-current voltage level;
selecting a gain value based on said assessing the direct-current voltage level; and
applying a gain using the selected gain value to an alternating-current component of the signal,
wherein said controlling the light output at the illumination assembly based on said assessing the direct-current voltage level is such that the alternating-current component of the signal is within a saturation level, upon said applying the gain.

11. The method of claim 10, further comprising:
determining that a measurement is a low perfusion measurement based on said assessing the direct-current voltage level, and wherein if there is a low perfusion measurement, the method further comprises controlling the light output to a lower intensity than that producing the present direct-current voltage level and selecting a large gain value as compared to normal measurements for said applying the gain.

12. The method of claim 11, wherein the large gain value is about 20 to 30 times.

13. The method of claim 10, wherein outputting light comprises using a red light source and/or an infra-red light source.

14. The method of claim 13, further comprising toggling the light sources on/off for the reflected output light to be detected as a single signal.

15. The method of claim 14, further comprising maintaining an amplitude difference between a maximum point and a minimum point of the single signal below a predetermined level by said controlling the light output at the illumination assembly.

16. The method of claim 15, wherein the predetermined level is obtained based on the alternating-current component of the signal being within the saturation level, upon said applying the gain.

17. The method of claim 16, further comprising:
using a summing amplifier to move the alternating-current component of the signal above a ground voltage level.

18. The method of claim 17, wherein the saturation level is based on an output of the summing amplifier.

19. A non-transitory computer readable data storage medium having stored thereon computer code means for instructing a microcontroller of an optical measurement device to execute a method for an optical measurement, the method comprising:
outputting light from two or more light sources to a surface portion of a user for measurement;
detecting the output light from the two or more light sources reflected from said surface portion of the user as a signal;
assessing a direct-current voltage level of the signal;
controlling the light output at the illumination assembly based on said assessing the direct-current voltage level;
selecting a gain value based on said assessing the direct-current voltage level; and
applying a gain using the selected gain value to an alternating-current component of the signal,
wherein said controlling the light output at the illumination assembly based on said assessing the direct-current voltage level is such that the alternating-current component of the signal is within a saturation level, upon said applying the gain.

20. The non-transitory computer readable data storage medium of claim 19, the method further comprising:
determining that a measurement is a low perfusion measurement based on said assessing the direct-current voltage level, and wherein if there is a low perfusion measurement, the method further comprises controlling the light output to a lower intensity than that producing the present direct-current voltage level and selecting a large gain value as compared to normal measurements for said applying the gain.

* * * * *